United States Patent [19]
Lucas et al.

[11] Patent Number: 5,731,153
[45] Date of Patent: Mar. 24, 1998

[54] IDENTIFICATION OF RANDOM NUCLEIC ACID SEQUENCE ABERRATIONS USING DUAL CAPTURE PROBES WHICH HYBRIDIZE TO DIFFERENT CHROMOSOME REGIONS

[75] Inventors: Joe N. Lucas, San Ramon; Tore Straume, Tracy; Kenneth T. Bogen, Walnut Creek, all of Calif.

[73] Assignee: The Regents of the University of California, Oakland, Calif.

[21] Appl. No.: 703,302

[22] Filed: Aug. 26, 1996

[51] Int. Cl.$^6$ .............................. C12Q 1/68; C07H 21/04
[52] U.S. Cl. ........................................... 435/6; 536/24.31
[58] Field of Search .................. 435/6, 810; 935/78; 536/24.31

[56] References Cited

U.S. PATENT DOCUMENTS

| | | | |
|---|---|---|---|
| 4,358,535 | 11/1982 | Falkow et al. | 435/5 |
| 4,376,110 | 3/1983 | David et al. | 436/513 |
| 4,478,914 | 10/1984 | Giese | 428/407 |
| 4,486,539 | 12/1984 | Ranki et al. | 436/504 |
| 4,894,325 | 1/1990 | Englehardt et al. | 435/6 |
| 5,273,882 | 12/1993 | Snitman et al. | 435/6 |
| 5,374,524 | 12/1994 | Miller | 435/6 |
| 5,424,413 | 6/1995 | Hogan et al. | 536/24.31 |

FOREIGN PATENT DOCUMENTS

| | | |
|---|---|---|
| 0 063 879 | 11/1982 | European Pat. Off. |
| 0 097 373 | 1/1984 | European Pat. Off. |
| 0 151 492 | 8/1985 | European Pat. Off. |
| WO 85/04674 | 10/1985 | WIPO |
| 94/10335 | 5/1994 | WIPO |

OTHER PUBLICATIONS

Funakoshi, et al., *J. of Chromatography* 638:21–27 (1993).
Gildea, et al., *Tetrahedron Letters* 31: 7095–7098 (1990).
Hobart, et al., *J. Immunological Methods* 153: 93–98 (1992).
Jayabaskaran, et al., *Preparative Biochemistry* 17(2): 121–141 (1987).
Leary, et al., *Proc. Natl. Acad. Sci. (U.S.A.)*, 80:4045–4049 (1983).
Lin, et al. *J. Org. Chem.* 56:6850–6856 (1991).
Lin, W.C., Ph.D. Theis, U.C. Riverside, (1990).
Lucas, et al., *International Journal of Radiation Biology* 56:35–44 (1989).
Lucas, et al., *International Journal of Radiation Biology*, 62: 53–63 (1992).
Mouton, et al., *Archives of Biochemistry and Biophysics* 218: 101–108 (1982).
Pinkel, et al., *Proc. Natl. Acad. Sci. (USA)* 85:9138–9142 (1988).
Pinkel, et al., *Proc. Natl. Acad. Sci. (USA)* 83:2934–2938 (1986).
Tkachuk, et al., *Science* 250: 559–562 (1990).

(List continued on next page.)

*Primary Examiner*—Kenneth R. Horlick
*Attorney, Agent, or Firm*—Henry P. Sartorio

[57] ABSTRACT

A method is provided for detecting nucleic acid sequence aberrations using two immobilization steps. According to the method, a nucleic acid sequence aberration is detected by detecting nucleic acid sequences having both a first nucleic acid sequence type (e.g., from a first chromosome) and a second nucleic acid sequence type (e.g., from a second chromosome), the presence of the first and the second nucleic acid sequence type on the same nucleic acid sequence indicating the presence of a nucleic acid sequence aberration. In the method, immobilization of a first hybridization probe is used to isolate a first set of nucleic acids in the sample which contain the first nucleic acid sequence type. Immobilization of a second hybridization probe is then used to isolate a second set of nucleic acids from within the first set of nucleic acids which contain the second nucleic acid sequence type. The second set of nucleic acids are then detected, their presence indicating the presence of a nucleic acid sequence aberration.

45 Claims, 9 Drawing Sheets

OTHER PUBLICATIONS

Vooijs, et al. *Am. J. Hum. Genet.* 52:586–597 (1993).
GIBCO BRL TRIzol™ Reagent (Life Technologies, Gaithersburg, M.D.).
The Strategene Catalog, p. 39 (1988).
Dunn et al., Cell., vol. 12, 23–26, Sep. 1977.
"Basic Methods in Molecular Biology", Ed. Davis et al., Elsevier Science Publ., pp. 75–78 (1986).
The Oncro Catalog (1992–1993).

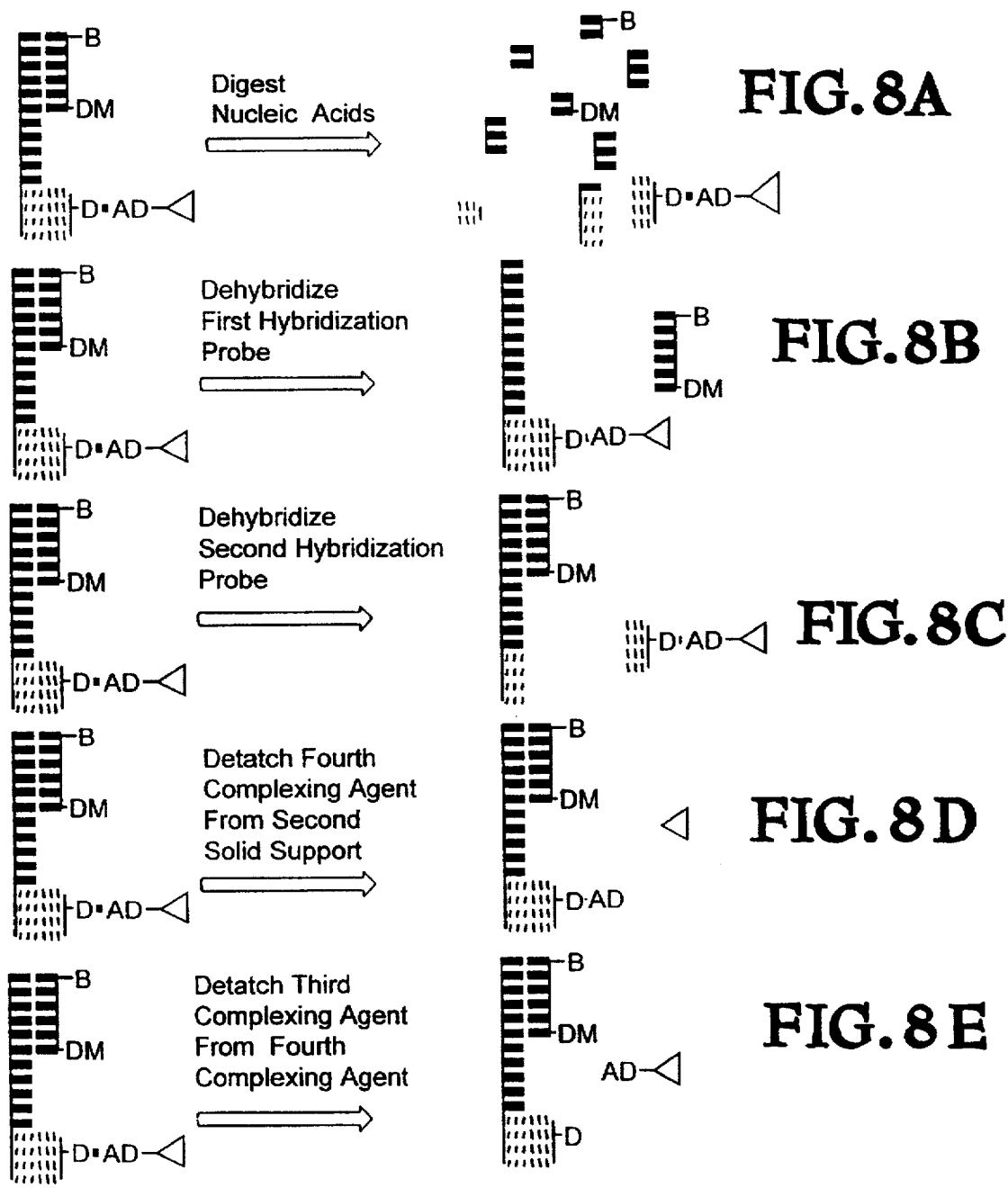
FIGURES 8A-E

D = Digoxigenin
AD = Antidigoxigenin
DM = Detectable Marker
B = Biotin
▬ = Chromosome type A
⁞⁞⁞⁞⁞⁞ = Chromosome type B

IDENTIFICATION OF RANDOM NUCLEIC ACID SEQUENCE ABERRATIONS USING DUAL CAPTURE PROBES WHICH HYBRIDIZE TO DIFFERENT CHROMOSOME REGIONS

The United States government has rights in this invention pursuant to Contract Number W-7405-ENG-48 between the United States Department of Energy and the University of California for the operation of Lawrence Livermore National Laboratory.

BACKGROUND OF THE INVENTION

1. Field of the Invention

The present invention relates to a method for identifying nucleic acid sequences using hybridization probes. More specifically, the present invention relates to a method for identifying and quantifying nucleic acid sequence aberrations using hybridization probes.

2. Description of Related Art

Hybridization probes are widely used to detect and/or quantify the presence of a particular nucleic acid sequence within a sample of nucleic acid sequences. Hybridization probes detect the presence of a particular nucleic acid sequence, referred to herein as a target sequence, through the use of a complimentary nucleic acid sequence which selectively hybridizes to the target nucleic acid sequence.

In order for a hybridization probe to hybridize to a target sequence, the hybridization probe must contain a nucleic acid sequence that is complementary to the target sequence. The complementary sequence must also be sufficiently long so that the probe exhibits selectivity for the target sequence over non-target sequences.

In order to design a hybridization probe that selectively hybridizes to a target sequence, one must first determine a nucleic acid sequence that is complementary to the target sequence. In applications where the target sequence is already known, for example, where one seeks to detect the insertion of a gene or promoter sequence into a vector or plasmid, a variety of methods are known for preparing highly selective hybridization probes. However, one limitation of hybridization assays is that one does not also know the target sequence in sufficient detail to prepare a selective hybridization probe.

Hybridization assays are most commonly designed to detect the presence or absence of a particular nucleic acid sequence, for example the insertion of a gene into a vector or plasmid. However, hybridization assays are generally not designed to detect the movement of a nucleic acid sequence relative to another nucleic acid sequences in a sample. The detection of nucleic acid sequence aberrations using a hybridization assay is limited by both the ability to design sequence specific probes and the ability to detect the movement of a nucleic acid sequence relative to other nucleic acid sequences in a sample. The detection of nucleic acid sequence aberrations is further limited by the infrequency of nucleic acid sequence aberrations. For example, chromosome translocations, a type of nucleic acid sequence aberration, is estimated to occur at a frequency on the order of 1 per 1,000,000 cells in a particular gene. Currently available hybridization assays are not able to accurately detect and quantify such infrequent genetic events. Although translocations are more frequent in the whole genome (approximately 1 per 200 cells), currently available assays are not practical for use in assaying the large number of individuals that must be evaluated in population studies.

As used herein, nucleic acid sequence aberrations refer to rearrangements between and within nucleic acids, particularly chromosomal rearrangements. Nucleic acid sequence aberrations also refer to the deletion of a nucleic acid sequence, particularly chromosome deletions. As used herein, the term "nucleic acids" refers to both DNA and RNA.

A chromosome translocation is an example of a nucleic acid sequence aberration. A chromosome translocation refers to the movement of a portion of one chromosome to another chromosome (inter-chromosome rearrangement) as well as the movement of a portion of a chromosome to a different location on that chromosome (intra-chromosome rearrangement). In general, chromosome translocations are characterized by the presence of a DNA sequence on a particular chromosome that is known to be native to a different chromosome or different portion of the same chromosome.

Chromosome translocations are frequently random genetic events which can occur at virtually any portion of any chromosome. Because the particular nucleic acid sequences involved in a chromosome translocation are not always known, it is generally not possible to design a hybridization probe that will uniquely identify a particular translocated sequence without first determining that translocated sequence. In addition, because chromosome translocations involve the movement of a nucleic acid sequence within a sample as opposed to the appearance or disappearance of the nucleic acid sequence, it generally is not possible to detect a chromosome translocation merely by assaying for the presence or absence of a particular nucleic acid sequence.

Chromosome translocations are known to be involved in carcinogenesis and inherited genetic disorders and have been shown to increase in frequency upon exposure to radiation and certain chemicals. Measurement of the frequency of chromosome translocations after exposure to radiation or a particular agent is therefore useful for evaluating the tendency of particular agents or forms of radiation to cause or increase the frequency of chromosome translocations.

Chromosome translocations are also known to be associated with specific diseases, including, for example lymphomas and leukemias, such as Burkitt's lymphoma, chronic myelocytic leukemia, chronic lymphocytic leukemia and granulocytic leukemia, as well as solid tumors such as malignant melanoma, prostate cancer and cervical cancer. A method for rapidly detecting a translocation associated with a disease is needed as a method for diagnosing disease.

Fluorescence in situ hybridization (FISH) using chromosome-specific composite hybridization probes ("chromosome painting") was developed as an assay for detecting chromosome translocations. FISH is described in Pinkel, et al., *Proc. Natl. Acad. Sci.* (USA) 83:2934–2938 (1986); Lucas, et al., *International Journal of Radiation Biology* 56:35–44 (1989), 62:53–63 (1992); Pinkel, et al., *Proc. Natl. Acad. Sci.* (USA) 85:9138–9142 (1988), each of which is incorporated herein by reference.

The fluorescent hybridization probes used in FISH-based chromosome painting are chromosome-specific but not unique, i.e., they hybridize primarily to a particular chromosome type. Chromosome translocations are identified in the FISH assay by visually scanning individual cells for the presence of two different fluorescent signals on a single chromosome, the two fluorescent signals originating from two different FISH probes, each probe having homology to a different chromosome type.

Because each FISH probe hybridizes to a specific chromosome type and not to the chromosome translocation itself, it is not possible to determine the frequency of chromosome translocations directly from the fluorescence signal emanating from a FISH probe. Rather, the frequency of random chromosome translocations in a cell sample must be determined according to FISH assays by visually scanning individual metaphase cells or slides. The need to visually scan such individual cells effectively limits the number of cells that can be assayed, thereby reducing the sensitivity of the FISH assay and introducing the possibility of human error.

Accordingly, a fast, accurate method is needed for quantifying chromosome translocations and other nucleic acid sequence aberrations. In particular, a method is needed which can analyze the nucleic acids contained in a sample of cells for the presence of a nucleic acid sequence aberration without the need to analyze each cell individually.

SUMMARY OF THE INVENTION

A two-step method is provided for detecting and quantifying the presence of nucleic acid sequences which include a nucleic acid sequence aberration, the nucleic acid sequence aberration being identified by the presence of nucleic acid sequences which include both a first and a second nucleic acid sequence type. The method is referred to as a two-step method because it involves two sequential immobilization steps.

In the first immobilization step of the method, a first set of nucleic acid sequences in a sample which include a nucleic acid sequence of a first type are immobilized using a first hybridization probe which includes a nucleic acid sequence which is complementary to nucleic acid sequences of the first type. By this step of the method, nucleic acid sequences which include a nucleic acid sequence of the first type are isolated from nucleic acid sequences in the sample which do not include a nucleic acid sequence of the first type.

In the second immobilization step of the method, a second set of nucleic acid sequences, corresponding to those nucleic acid sequences which were isolated in the first immobilization step which also include a nucleic acid sequence of a second type, are immobilized using a second hybridization probe which includes a nucleic acid sequence which is complementary to nucleic acid sequences of the second type. Thus, through the first and second immobilization steps, nucleic acid sequences are selectively immobilized which contain a nucleic acid sequence aberration, characterized by their having nucleic acid sequences of both a first and a second nucleic acid sequence type. Once isolated, these sequences may be detected, quantified and/or characterized.

More specifically, the first immobilization step of the method includes contacting a sample of nucleic acids with a first hybridization probe under conditions favorable for first hybridization probe such that the first hybridization probe hybridizes to a first set of nucleic acids which include the nucleic acid sequence of the first type. The first hybridization probe may be immobilized on a first solid support before hybridization or after hybridization of the first hybridization probe to the nucleic acids in the sample. According to the method, the sample may also be contacted with the second hybridization probe during the first immobilization step or during the second immobilization step.

After the first immobilization step, the performance of which serves to immobilize the first set of nucleic acids hybridized to the first hybridization probe, the first set of nucleic acids are released from the first solid support and thus isolated.

During the second immobilization step, a second set of nucleic acids are immobilized which correspond to those nucleic acids of the first set which also hybridize to the second hybridization probe. Immobilization of the second set is performed using a second hybridization probe which is immobilized on a second solid support. As discussed above, hybridization of the nucleic acids in the sample to the second hybridization probe may be performed during the first immobilization step, before, after or while the first hybridization probe is hybridized to the nucleic acids in the sample. Alternatively, hybridization of nucleic acids in the sample to the second hybridization probe may be performed during the second immobilization step, either before or after the second hybridization probe is immobilized on the second solid support.

Once the second set of nucleic acids have been immobilized, the second set of nucleic acids are detected, the presence of which indicate the presence of a nucleic acid sequence aberration. Once immobilized, the second set of nucleic acids may also be quantified and/or characterized, depending on the application.

According to the method, the first hybridization probe is preferably attached to the first solid support by a linkage which is detachable, the step of releasing the first set of nucleic acids preferably including detaching the detachable linkage. The linkage attaching the second hybridization probe to the second solid support is also preferably detachable.

The first hybridization probe preferably includes a detectable marker which may be used to detect the second set of nucleic acids. The presence of the second set of nucleic acids may also be detected by releasing the second set of nucleic acids from the second solid support. Detection of the second set of nucleic acids may also include amplification and/or purification of the second set of nucleic acids.

The method for detecting nucleic acid sequence aberrations may be used to diagnose diseases whose occurrence is associated with the occurrence of the nucleic acid sequence aberration being detected. Examples of diseases that may be detected include cancers such as leukemia, lymphoma, melanoma, prostate cancer and cervical cancer.

BRIEF DESCRIPTION OF THE DRAWINGS

FIGS. 1–8 depict exemplary methods for detecting a chromosome translocation.

FIG. 1 depicts the isolation of DNA from a sample of cells, hybridization of the DNA to a first hybridization probe, immobilization of the hybridized DNA on a first solid support and a first separation step.

FIG. 2 depicts the isolation of DNA from a sample of cells, hybridization of the DNA to a first hybridization probe which is immobilized on a first solid support and a first separation step.

FIG. 3 depicts the isolation of DNA from a sample of cells, hybridization of the DNA to first and second hybridization probes, immobilization of the hybridized DNA on a first solid support and a first separation step.

FIG. 4 depicts the isolation of DNA from a sample of cells, hybridization of the DNA to first and second hybridization probes, immobilization of the first hybridization probe on a first solid support and a first separation step.

FIG. 5 depicts the release of the immobilized DNA from the first solid support, the hybridization of the released DNA to a second hybridization probe, the immobilization of the second hybridization probe and a second separation step.

FIG. 6 depicts the release of the immobilized DNA from the first solid support, the hybridization the released DNA to a second hybridization probe immobilized on a second solid support and a second separation step.

FIG. 7 depicts the release of the immobilized DNA from the first solid support, the immobilization of the second hybridization probe and a second separation step.

FIGS. 8A–G depict several approaches to isolating and/or detecting a detectable marker on the immobilized first hybridization probe. FIG. 8A illustrates the detectable marker being separated from the solid support by digesting the nucleic acids immobilized on the solid support.

FIG. 8B illustrates the detectable marker being separated from the solid support by the dehybridization of the first hybridization probe.

FIG. 8C illustrates the detectable marker being separated from the solid support by the dehybridization of the second hybridization probe.

FIG. 8D illustrates the detectable marker being separated from the solid support by detaching the fourth complexing agent from the solid support.

FIG. 8E illustrates the detectable marker being separated from the solid support by detaching the third and fourth complexing agents.

FIG. 8F illustrates the detectable marker being separated from the solid support by detaching the third complexing agent from the second hybridization probe.

FIG. 8G illustrates the detectable marker being separated from the solid support by detaching the detectable marker from the; first hybridization probe.

DETAILED DESCRIPTION OF THE INVENTION

Figure 1:
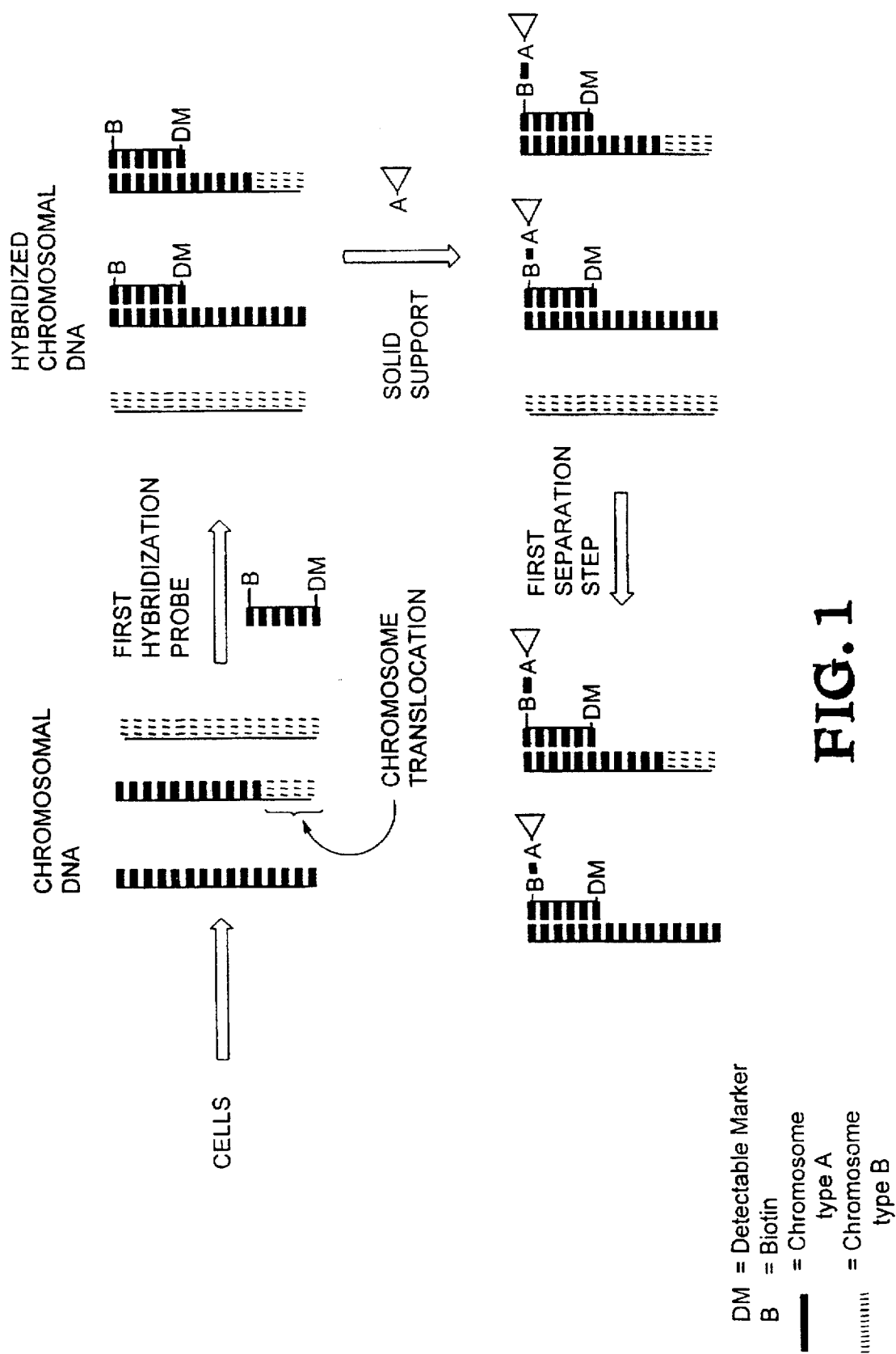

The present invention relates to a two-step method for detecting nucleic acid sequence aberrations. As used herein, the term "nucleic acid sequence aberration" refers to rearrangements between and within nucleic acid sequences, particularly chromosomes. Nucleic acid sequence aberration also refers to the deletion of a nucleic acid sequence, particularly chromosome deletions. As used herein, the term "nucleic acids" refers to DNA and RNA of any origin.

According to the method of the present invention, a nucleic acid sequence aberration is detected by detecting nucleic acid sequences having both a first nucleic acid sequence type (e.g., from a first chromosome) and a second nucleic acid sequence type (e.g., from a second chromosome), the presence of the first and the second nucleic acid sequence type on the same nucleic acid sequence indicating the presence of a nucleic acid sequence aberration.

The method is referred to as a two-step method because it involves two sequential immobilization steps. The first immobilization step is conducted by isolating those nucleic acid sequences in a sample having a first nucleic acid sequence type using a first hybridization probe and a first solid support. In the first immobilization step, a first set of nucleic acid sequences which include nucleic acid sequences of the first type are immobilized from the sample using a first hybridization probe which includes a nucleic acid sequence which is complementary to nucleic acid sequences of the first type. The first hybridization probe immobilizes the first set of nucleic acids by itself being immobilized to a first solid support, either before or after hybridization of the first hybridization probe to the first set of nucleic acids. By this step of the method, this first set of nucleic acid sequences which include a nucleic acid sequence of the first type are isolated from nucleic acid sequences in the sample which do not include a nucleic acid sequence of the first type.

In the second immobilization step of the method, a second set of nucleic acid sequences are immobilized from the set of nucleic acid sequences which were isolated in the first immobilization step which also include a nucleic acid sequence of a second type. A second hybridization probe, which includes a nucleic acid sequence which is complementary to nucleic acid sequences of the second type, is used to immobilize the second set of nucleic acids. Hybridization of the second hybridization probe to nucleic acids in the sample may be performed during the first or second immobilization steps. When hybridization of the second hybridization probe is performed during the second immobilization step, immobilization of the second hybridization probe to the second solid support may be performed either before or after hybridization of the second hybridization probe.

According to the method, the first hybridization probe includes a nucleic acid sequence that is complementary to a first nucleic acid sequence type such that the first hybridization probe hybridizes to nucleic acid sequences containing the first nucleic acid sequence type. The first hybridization probe and first solid support are also designed such that the first hybridization probe is releasably attachable to the first solid support, attachment of the hybridization probe to the solid support enabling sequences hybridized to the hybridization probe to be immobilized.

According to the method, a sample of nucleic acid sequences is contacted with a first hybridization probe under conditions favorable for hybridization. The first hybridization probe is immobilized to the first solid support, either before or after hybridization of the first hybridization probe to the sample of nucleic acid sequences. Only nucleic acid sequences in the sample that include a nucleic acid sequence of the first type are isolated through immobilization to the first solid support. The sequences isolated using the first hybridization probe are referred to as the first set of nucleic acids. Nucleic acid sequences that do not include a first nucleic acid sequence type do not become immobilized to the first solid support and thus may be eliminated from the sample.

After the non-immobilized nucleic acid sequences have been eliminated, the first set of nucleic acids, some of which may also include a nucleic acid sequence of a second type, are isolated. Since all sequences in the first set of nucleic acids include a nucleic acid sequence of the first type, any sequences in the first set of nucleic acids which also include a nucleic acid sequence of the second type correspond to nucleic acid sequences having a nucleic acid sequence aberration.

According to the method, the first set of nucleic acids are released from the first solid support and subjected to a second immobilization step in order to immobilize a second set of nucleic acids (i.e., those sequences in the first set of nucleic acids that hybridize to the second hybridization probe).

A second hybridization probe and a second solid support are used in the second immobilization step. The second hybridization probe may be hybridized to the nucleic acids in the sample during either the first or second immobilization step. When the second hybridization probe is hybridized to the nucleic acids in the sample during the first immobilization step, the second hybridization probe will be hybridized to those nucleic acids of the first set which also include a nucleic acid sequence of the second type. By then immobilizing the second hybridization probe during the second immobilization step, the second set of nucleic acids are immobilized.

The second hybridization probe may also be hybridized to the nucleic acids in the sample during the second immobilization step. In this instance, the second hybridization may be immobilized to the second solid support either before or after hybridization of the second hybridization probe.

According to the present invention, only nucleic acid sequences containing the first nucleic acid sequence type, i.e. nucleic acid sequences which hybridize to the first hybridization probe, will be isolated using the first hybridization probe and first solid support. Of this first set of nucleic acids, only those nucleic acid sequences containing the second nucleic acid sequence type will hybridize to and be immobilized by the second hybridization probe. Thus, after the second immobilization step, the amount of first hybridization probes and/or nucleic acid sequences immobilized on the second solid support is proportional to the number of nucleic acid sequences having both first and second sequence types. When the first and second nucleic acid sequence types are selected such that the presence of both sequence types indicate the presence of a nucleic acid sequence aberration, the method of the present invention may be used to isolate nucleic acid sequences in a sample having a nucleic acid sequence aberration.

Nucleic acid sequences in a sample having a nucleic acid sequence aberration can be detected and/or quantified by detecting the presence of the first hybridization probes and/or the nucleic acid sequences immobilized on the second solid support. The second hybridization probe is preferably designed to be releasably attachable to a second solid support. This enables the nucleic acid sequences and first hybridization probes immobilized on the second solid support to be isolated by detachment from the second solid support. Once isolated, the sequences can be purified, characterized, amplified and/or quantified.

Detection and/or quantification of the first hybridization probes and/or immobilized nucleic acid sequences may be performed, for example, by incorporating a detectable marker onto some or all of the first hybridization probe or the nucleic acid sequences being analyzed. Alternatively, the first hybridization probe and/or immobilized nucleic acid sequences may be quantified by standard spectroscopic and chromatographic techniques known in the art for quantifying nucleic acids.

The method of the present invention increases by several fold the sensitivity, precision and speed of detecting randomly occurring nucleic acid sequence aberrations such as chromosome translocations over current detection methods including FISH assays. For example, FISH assays require visually scanning individual cells. By contrast, the method of the present invention enables the frequency of nucleic acid sequence aberrations such as chromosome translocations to be quantified by immobilizing and isolating the nucleic acid sequences having the nucleic acid sequence aberration. As a result, the frequency of the aberration can be determined by quantifying the isolated pool of nucleic acid sequences or hybridization probes bound thereto. By analytically detecting a pool of nucleic acids as opposed to visually scanning individual cells, one is able to routinely analyze over a thousand times as many cells for aberrations as was previously feasible using the FISH assay. This large increase in the number of cells that may be analyzed at a time significantly enhances the speed, sensitivity and accuracy of nucleic acid sequence aberration detection. For example, it permits the measurement of nucleic acid sequence aberrations in large populations evaluated epidemiologically. This is not practical using current FISH technology.

Another application of the method of the present invention is the evaluation of clastogentic agents, such as radiation and certain chemicals, for their tendency to increase the frequency of nucleic acid sequence aberrations.

The method of the present invention may also be readily adapted for the diagnosis of disease, the occurrence of which is associated with and/or identifiable by the presence of a particular nucleic acid sequence aberration. In particular, diseases, such as cancer and genetic disorders, which are associated with and/or identifiable by the presence of a particular nucleic acid sequence aberration can be identified using the method. For example, the translocation of oncogene c-myc, which is normally located on chromosome 8q to chromosome 14, referred to as a t(8;14) translocation, is characteristic of Burkitt's lymphoma. Using the method of the present invention for detecting aberrations, diseases such as Burkitt's lymphoma may be readily diagnosed. Further, given the large number of cells that can be evaluated using the present method, very low translocation frequencies can be measured. Thus, the method of the present invention represents a valuable tool for the early detection of disease.

Examples of diseases that may be detected according to the method of the present invention include, but are not limited to lymphomas and leukemias, such as Burkitt's lymphoma which is identifiable by a unique translocation between chromosomes 8 and 14, chronic myelogenous leukemia which is identifiable by a unique translocation between chromosomes 9 and 22, chronic lymphocytic leukemia which is identifiable by a unique translocation between chromosomes 11 and 14 and granulocytic leukemia which involves granulocytes which cannot be cultured, t(8;21). Unique translocations may also be identified in solid tumors, such as, malignant melanoma, t(1:19)(q12:q13), prostate cancer t(8:12) and cervical cancer, t(1.8) (q22:p23.1) and t(1:5)(q25:p32). Further, as new diseases are linked to the occurrence of a nucleic acid sequence aberration, these new diseases will also be rapidly detectable using the method of the present invention.

Using the method of the present invention, diseased cells, such as cancer cells can be rapidly detected. Further, because a relatively large number of cells can be assayed at a time with a high level of sensitivity, the method of the present invention provides an effective tool for detecting these diseases related to progenitor cells at an early stage, when medical intervention may succeed in preventing disease progression.

The present invention also relates to a kit for detecting nucleic acid aberrations and diagnosing disease according to the methods of the present invention. In general, the kits of the present invention include a first hybridization probe, a second hybridization probe, a first solid support, and a second solid support as described herein. Optionally, the kits may also include instructions describing how to use the kit to detect nucleic acid sequence aberrations and the diagnosis of disease associated with or identifiable by the presence of a particular nucleic acid sequence aberration.

Specific examples of disease diagnosis kits that may be prepared according to the present invention include kits for diagnosing malignancies such as Burkitt's lymphoma, chronic myelocytic leukemia, chronic lymphocytic leukemia, granulocytic leukemia, malignant melanoma, prostate cancer, and cervical cancer.

The method will now be discussed in greater detail making reference to the figures. The first step of the method involves obtaining a sample of nucleic acid sequences to be analyzed. As illustrated in FIG. 1, in applications when the sample of nucleic acid sequences consists of chromosomal DNA, the chromosomal DNA is first isolated from a sample of cells. Chromosomal DNA may be isolated by any of the variety of methods known in the art. For example, the chromosomal DNA may be isolated by the method taught in Vooijs, et al. *Am. J. Hum. Genet.* 52:586–597 (1993) or by using the GIBCO BRL TRIzol™ Reagent (Life Technologies, Gaithersburg, Md.), each of which is incorporated herein by reference.

Chromosomal DNA may be analyzed as whole chromosomes, chromosome fragments or chromosomal DNA fragments, all of which are hereinafter referred to as chromosomal DNA. When analyzing chromosomal DNA for the presence of nucleic acid sequence aberrations, the chromosomal DNA may be organized as an extended double strand, as extended nucleosomes, as chromatin fiber, as folded fiber, and as interphase, prophase or metaphase DNA. Sandberg, "The chromosomes in human cancer and leukemia", Elsevier; New York (1980), pp. 69–73.

The preferred chromosome organization for assaying chromosomal DNA for the presence of a nucleic acid sequence aberration depends on the number of nucleic acid bases separating the first and second nucleic acid sequence types being recognized by the first and second hybridization probes identifying the aberration. The preferred size of the solid support, if a particulate solid support such as beads are employed, is a function of the size of the piece of target DNA or RNA to be evaluated. For example, the nucleic acid sequences being analyzed can range in size from less than a micron to several millimeters in length depending on the level of organization used and the degree to which the chromosomes are fractionated. For example, detection of the Philadelphia chromosome would require target pieces on the order of a few hundred kilobases (less than 1 mm) if the DNA molecules are fully extended and only a few microns if the chromosomes are in the interphase level of organization.

A series of different embodiments of the two-step method are illustrated with regard to the figures. As illustrated in FIG. 1, once the sample of nucleic acids is obtained, the nucleic acid sample may be contacted with a first hybridization probe under conditions favorable for hybridization. The first hybridization probe is specific for a first nucleic acid sequence type, i.e., it is complementary to the first nucleic acid sequence type and therefore selectivity hybridizes to that nucleic acid sequence type.

In the case of detecting chromosomal translocations, the first hybridization probe is preferably a chromosome-specific probe such that it selectivity hybridizes to a particular chromosome type. In the case of detecting inter-chromosomal rearrangements, "chromosome type" refers to individual chromosomes. In the case of detecting intra-chromosomal rearrangements, "chromosome type" refers to different portions of an individual chromosome since intra-chromosomal rearrangements involve the movement of a sequence to a different portion of the same chromosome.

Any hybridization probe which preferentially hybridizes to a particular nucleic acid sequence may be used as the first hybridization probe and is intended to fall within the scope of the present invention. In the case of detecting chromosome translocations, an exemplary method for preparing PCR libraries of individual chromosomes and the use of those libraries to prepare chromosome-specific hybridization probes is taught in Vooijs, et al. *Am. J. Hum. Genet.* 52:586–597 (1993) which is incorporated herein by reference.

The first hybridization probe does not by itself detect the nucleic acid sequence aberration. Rather, the first hybridization probe is selective for a first nucleic acid sequence type and hybridizes to all nucleic acid sequences containing the first nucleic acid sequence type, regardless of whether a nucleic acid sequence aberration is present. For example, with regard to detecting chromosome translocations, the first hybridization probe may be a chromosome specific probe.

The method of the present invention relies on a second hybridization probe to isolate those nucleic acid sequences isolated by the first hybridization probe which also have a nucleic acid sequence of a second type. In most prior art hybridization assays using two hybridization probes, the first hybridization probe serves to isolate the nucleic acid being detected while the second hybridization probe serves to enable detection of the nucleic acid sequence isolated by the first hybridization probe. Hence, in most prior art hybridization assays, the second hybridization probe does not generally perform a separate isolation function. As illustrated in FIG. 1, the first hybridization probe includes a biotin molecule (B) which, as described herein, is used to immobilize the probe. The probe also includes a detectable marker (DM) for later detecting the nucleic acid aberrations.

Figure 2:
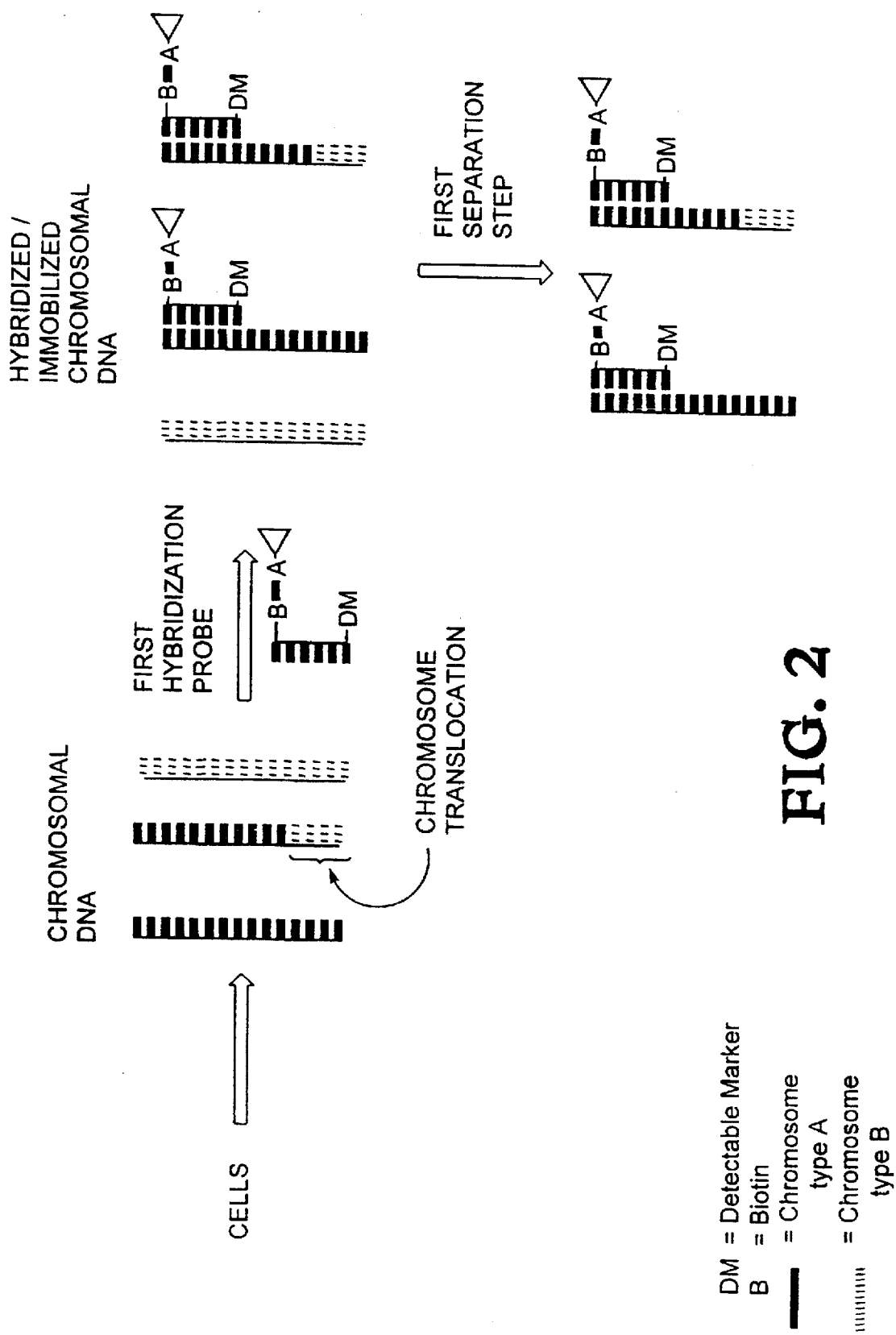

As further illustrated in FIG. 1, after hybridization of the first hybridization probe to a sample of nucleic acids, the first hybridization probe is immobilized onto a first solid support. Alternatively, as illustrated in FIG. 2, the first hybridization probe may be immobilized onto the first solid support prior to hybridization to the sample of nucleic acids. However, it is preferred that the first hybridization probe be immobilized after hybridization since hybridization is generally more effectively conducted in solution.

Figure 3:
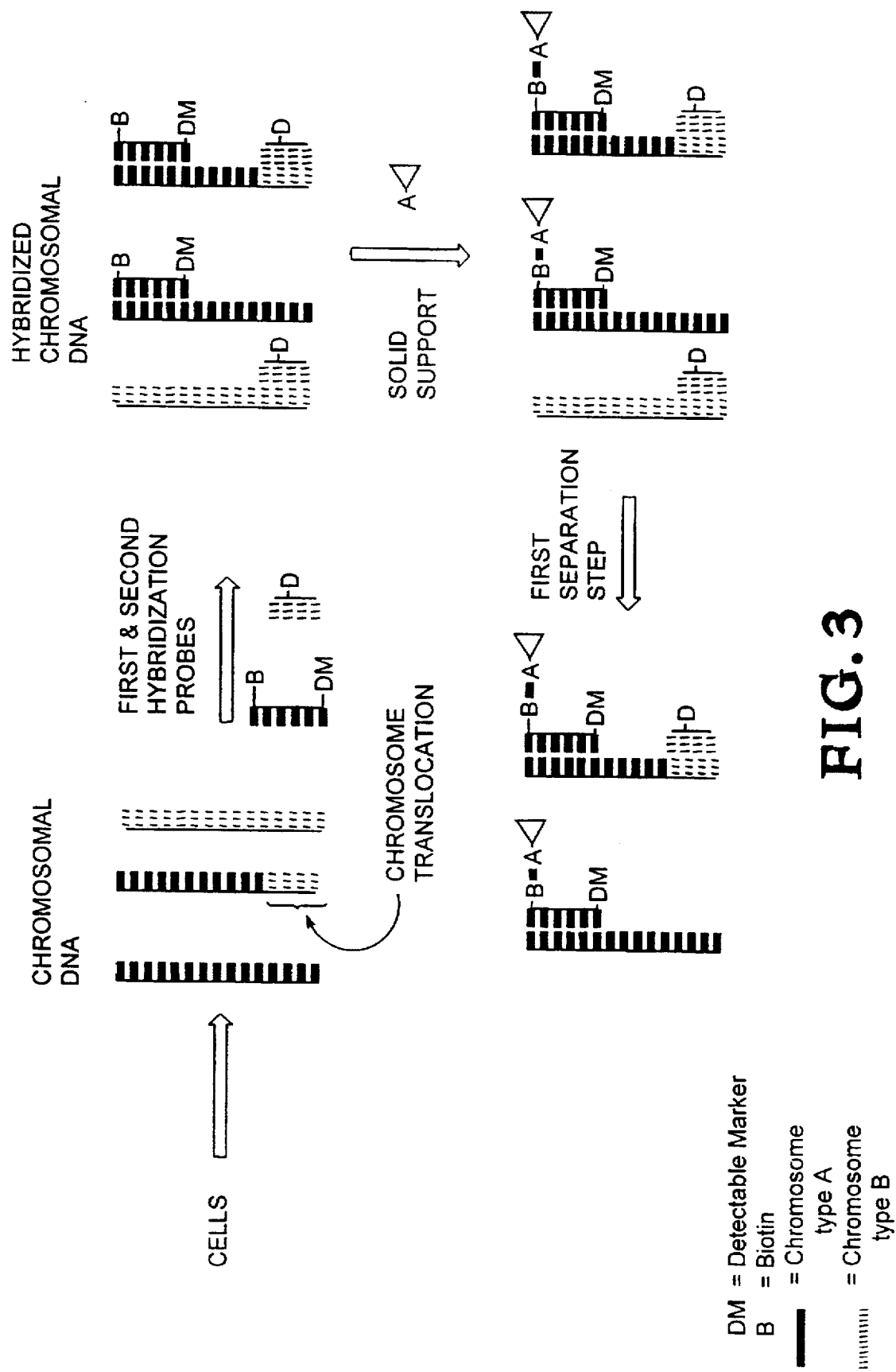
Figure 4:
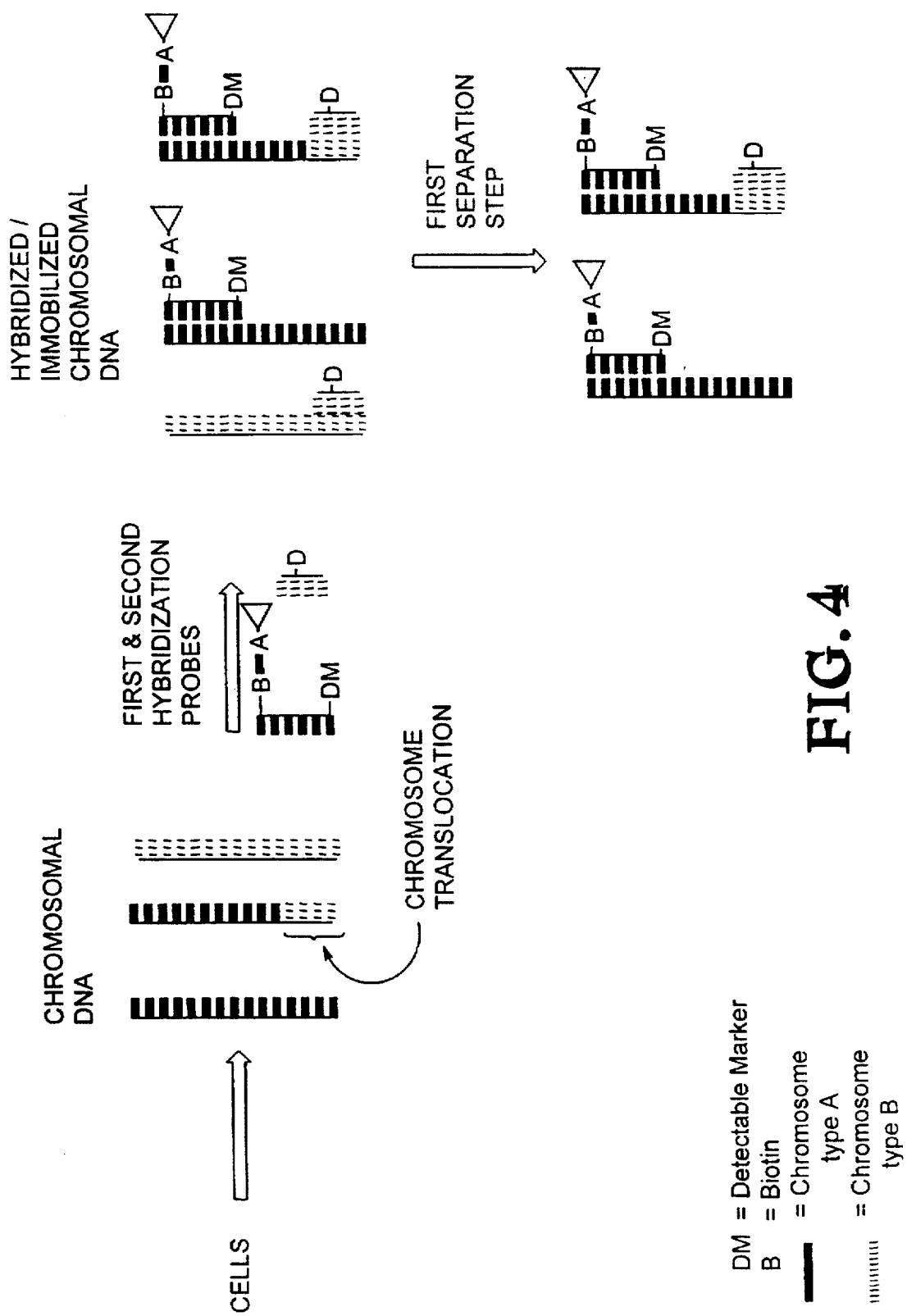

As illustrated in FIGS. 3 and 4, hybridization of the first hybridization probe may be performed in the presence of a second hybridization probe which itself hybridizes to nucleic acid sequences of the second type. Although FIGS. 3 and 4 illustrate the hybridization of the second hybridization probe in the presence of the first hybridization probe, it should also be understood that the second hybridization probe may be hybridized during the first immobilization step either before or after hybridization of the first hybridization probe.

When the first hybridization probe is immobilized on the first solid support after hybridization, as illustrated in FIGS. 1 and 3, it is preferred that the first hybridization probe be attached to the first solid support using a pair of complexing agents where the first hybridization probe includes a first complexing agent that forms a binding pair with a second complexing agent on the first solid support, thereby enabling the immobilization of the first hybridization probe onto the solid support.

The first and second complexing agents used to attach the first hybridization probe to the first solid support may be any pair of complexing agents which form a strong binding pair. Since elevated temperatures are generally required for hybridization, the binding pair should preferably be stable at temperatures at least up to about 37° C.

Examples of suitable binding pairs of complexing agents include antibody-antigen pairs, biotin-avidin and digoxigenin-anti-digoxigenin. Avidin-biotin and analogues and derivatives thereof are particularly preferred as binding pairs due to their enhanced thermal stability. Examples of avidin derivatives include, but are not limited to, streptavidin, succinyl avidin, ferritin avidin, enzyme avidin and cross-linked avidin. Examples of biotin derivatives include, but are not limited to caproylamidobiotin and biocytin. Examples of biotin analogues include, but are not limited to desthiobiotin and biotin sulfone. Biotin-antibiotin antibody is an example of a suitable antibody-antigen pair. The binding pair of biotin and avidin are illustrated in FIGS. 1–4.

Any solid support to which a complexing agent may be attached may be used in the present invention. Examples of suitable solid support materials include, but are not limited to, silicates such as glass and silica gel, cellulose and nitrocellulose papers, nylon, polystyrene, polymethacrylate, latex, rubber, and fluorocarbon resins such as TEFLON™.

The solid support material may be used in a wide variety of shapes including, but not limited to slides and beads. Slides provide several functional advantages and thus are a preferred form of solid support. Slides can be readily used with any chromosome organization. Due to their flat surface, probe and hybridization reagents can be minimized using glass slides. Slides also enable the targeted application of reagents, are easy to keep at a constant temperature, are easy to wash and facilitate the direct visualization of DNA immobilized on the solid support. Removal of DNA immobilized on the solid support is also facilitated using slides. It is estimated that a standard microscope glass slide can contain 50,000 to 100,000 cells worth of DNA. Beads, such as BioMag® Strepavidin magnetic beads are another preferred form of solid support containing a second complexing agent.

It is preferred that avidin or an avidin derivative be used as the second complexing agent. Avidin may be chemically attached to glass using the N-hydroxysuccinamide active ester of avidin as taught by Manning, et al. *Biochemistry* 16:1364–1370 (1977) and may be attached to nylon by a carbodiimide coupling as taught by Jasiewicz, et al. *Exp. Cell Res.* 100:213–217 (1976). Magnetic microbeads labled with avidin and strepavidin labeled bead may be obtained from Advanced Magnetics, Inc., Cambridge, Mass. and from Spherotech, Inc;., Libertyville, Ill.

As illustrated in FIGS. 1–4, once nucleic acids which include a first nucleic acid sequence type have been hybridized to the first hybridization probe and immobilized on the solid support, the hybridized nucleic acids are separated from any non-hybridized nucleic acids in a first separation step. Separation of the hybridized nucleic acids from non-hybridized nucleic acids may be accomplished by a variety of methods known in the art including, but not limited to, centrifugation, filtration and washing.

Only nucleic acid sequences in the sample that include a nucleic acid sequence of the first type are isolated through immobilization to the first solid support. Nucleic acid sequences that do not include a first nucleic acid sequence type do not become immobilized to the first solid support and are eliminated from the sample by the first separation step.

Figure 5:
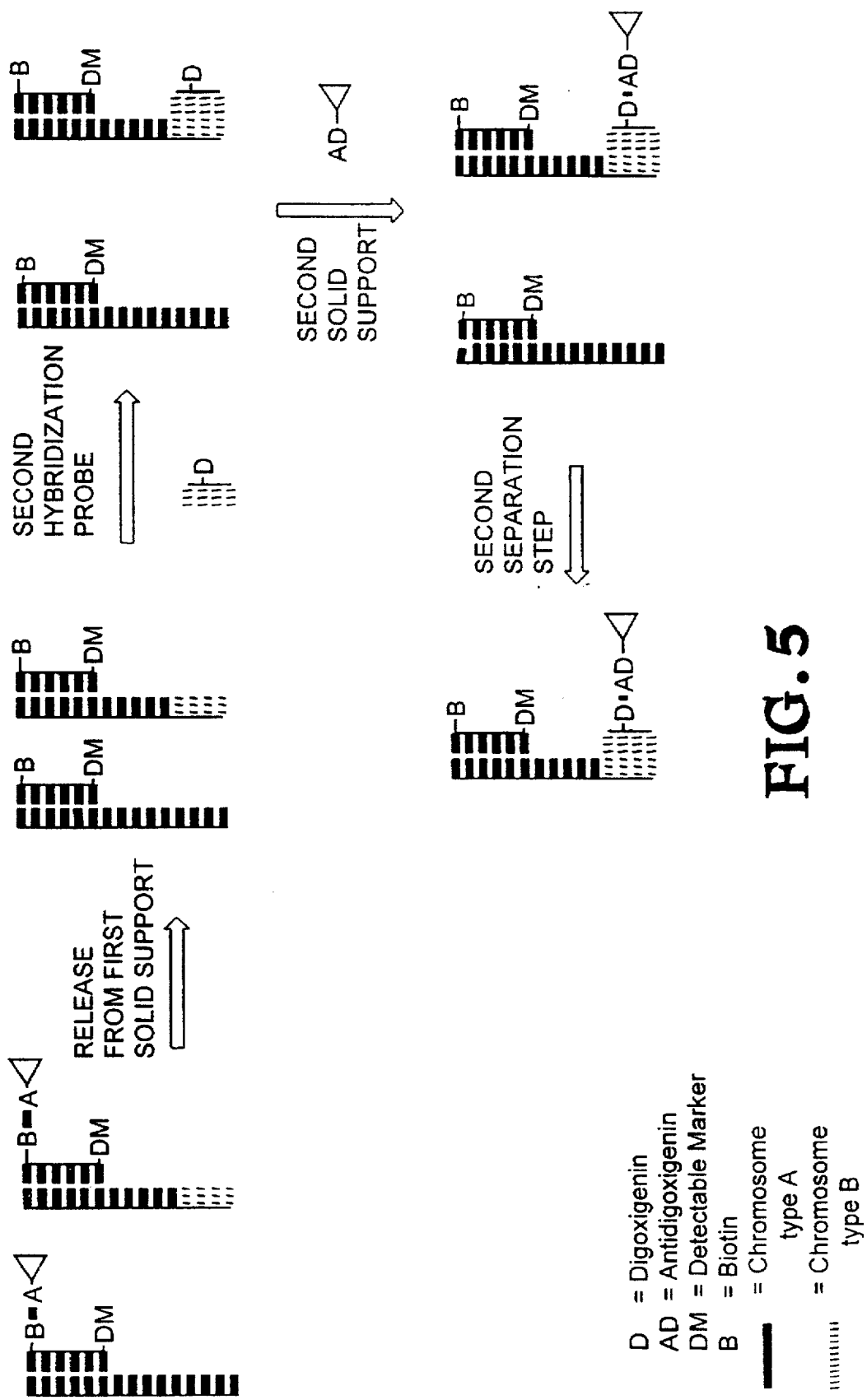
Figure 6:
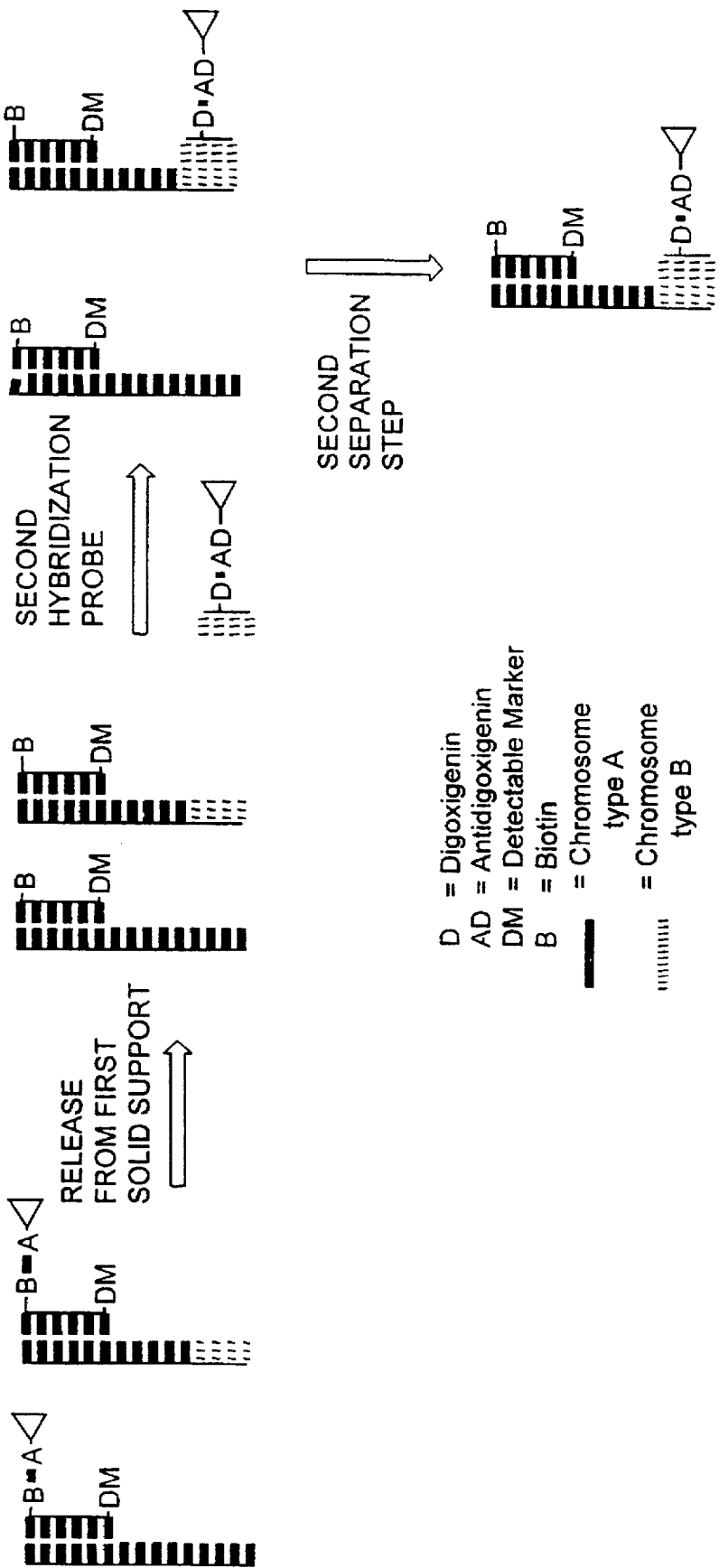
Figure 7:
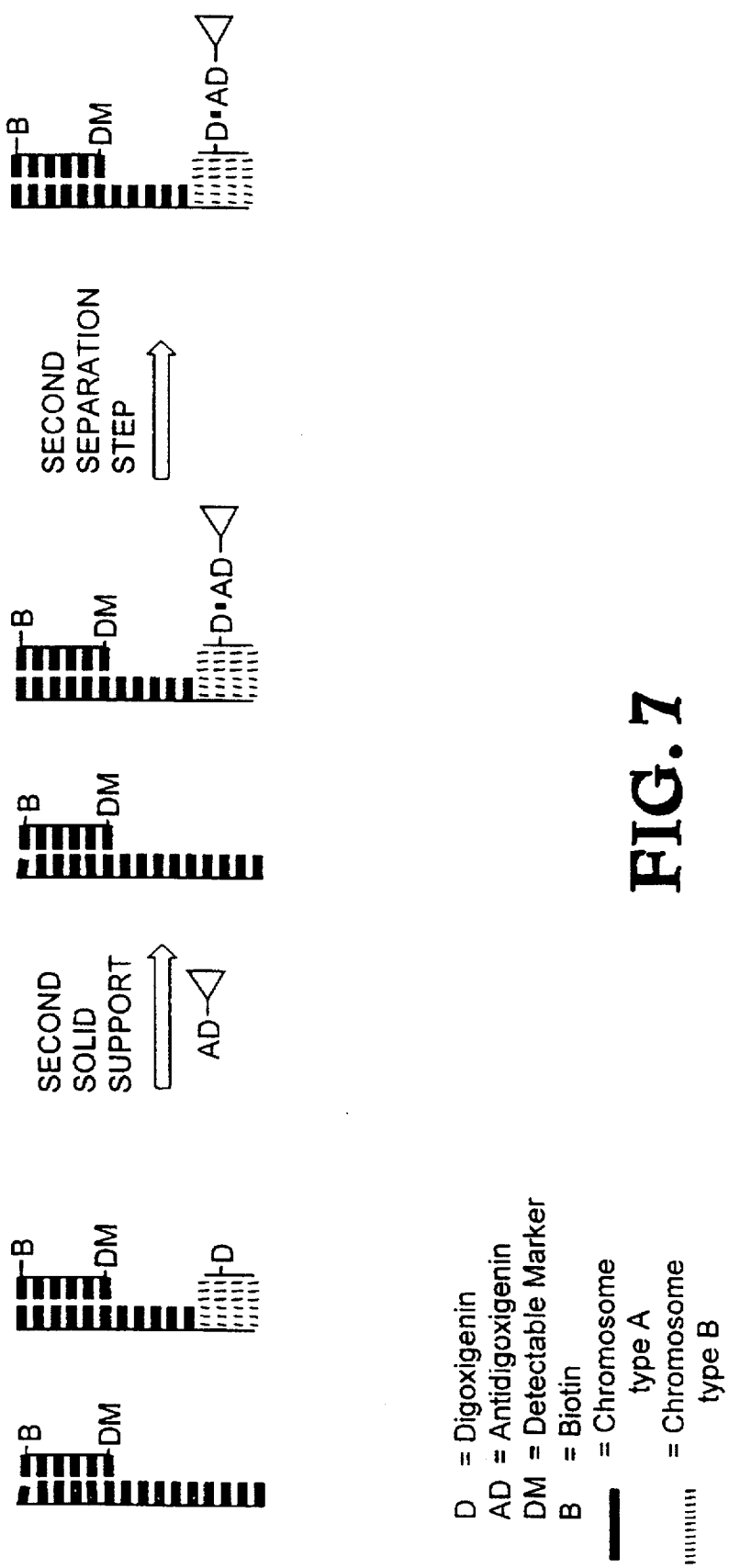

As illustrated in FIGS. 5–7, the first hybridization probe is releasably attached to a first solid support. This enables the first set of nucleic acids immobilized on the first solid support to be released after the first separation step. Releasable attachment of the first hybridization probe to the first solid support may be accomplished by the incorporation of a detachable linkage between the first hybridization probe and the first solid support, for example, between the first hybridization probe and the first complexing agent, between the first solid support and the second complexing agent, or between the first and second complexing agents. Examples of suitable detachable linkages include, but are not limited to the detachable linkers described in Lin, et al., *J. Org. Chem.* 56:6850–6856 (1991); Ph.D. Thesis of W.-C. Lin, U. C. Riverside, (1990); Hobart, et al., *J. Immunological Methods* 153:93–98 (1992); Jáyabaskaran, et al., *Preparative Biochemistry* 17(2): 121–141 (1987); Mouton, et al., *Archives of Biochemistry and Biophysics* 218:101–108 (1982); Funkakoshi, et al., *J. of Chromatography* 638:21–27 (1993); Gildea, et al., *Tetrahedron Letters* 31:7095–7098 (1990); and WO 85/04674, each of which are incorporated herein by reference.

As illustrated in FIGS. 5 and 6, once any non-hybridized nucleic acids have been removed, the first set of nucleic acids are; contacted with a second hybridization probe under conditions favorable for hybridization.

As illustrated in FIGS. 3 and 4, hybridization to the second hybridization probe may be performed during the first immobilization step. As a result, only immobilization of the second hybridization probe needs to be performed during the second immobilization step. However, the first immobilization step serves to eliminate nucleic acids that do not contain a nucleic acid sequence of the first type, particularly nucleic acid sequences of the second type that do not also contain a nucleic acid sequence of the first type. By eliminating nucleic acid sequences of the second chromosome type that do not also contain a nucleic acid sequence of the first type prior to introducing the second hybridization probe, the second hybridization probe only binds to sequences having a nucleic acid aberration. Thus, by hybridizing the second hybridization probe after the first immobilization step, less nucleic acid sequences which do not contain an aberration are present which can bind to the second hybridization probe. In addition, less second hybridization probe is needed. Both of these factors aid in minimizing the amount of second hybridization probe that is not bound to a nucleic acid sequence aberration. This serves to minimize the amount of background noise present in the assay, thereby enabling greater assay accuracy and lower detection limits.

The second hybridization probe includes a nucleic acid sequence that does not hybridize to nucleic acids of the same type as the first hybridization probe. Any nucleic acid sequence which does not hybridize to the first nucleic acid sequence type may be used in the second hybridization probe and is intended to fall within the scope of the present invention.

In one embodiment of the method, the second hybridization probe may hybridize to more than one chromosome type other than the chromosome type to which the first hybridization probe hybridizes. In this embodiment, the second hybridization probe enables the rapid identification of all nucleic acid sequence aberrations involving the chromosome identified by the first hybridization probe.

Where possible, the second hybridization probe preferably includes a nucleic acid sequence that is uniquely specific to the nucleic acid sequence aberration being detected. The use of uniquely specific hybridization sequences is preferred since it minimizes the occurrence of background noise due to non-specific binding. For example, when detecting particular nucleic acid sequence aberrations, the second hybridization probe is preferably specific for a particular nucleic acid sequence. For example, some diseases, such as cancer and genetic disorders appear to arise from a specific chromosome translocation. By using a second hybridization probe that is specific for a nucleic acid sequence, the translocation of which is associated with a particular disease, it is possible to rapidly identify the presence of chromosome translocations associated with the disease to be diagnosed. It is also preferred to employ a composite second hybridization probe which includes a series of sequences that are all either unique or chromosome specific for the aberration being detected.

Non-specific binding by non-unique first and/or second hybridization probes to the nucleic acid sample may be minimized through the use of suppression techniques such as is disclosed by Pinkel, et al. Proc. Natl. Acad. Sci. USA (1988) 85:9138–9142 which is incorporated herein by reference. As taught in Pinkel, et al. unlabeled nucleic acid probes, for example, unlabeled genomic DNA, may be used to competitively inhibit non-specific hybridization.

When detecting random nucleic acid sequence aberrations, such as random chromosomal translocations, the first and/or second hybridization probe is preferably a composite chromosome hybridization probe capable of hybridizing along the entire length of a chromosome other than the chromosome to which the second hybridization probe hybridizes. By using a composite hybridization probe, multiple hybridization probes can be used. Each of the multiple hybridization probes can be designed to incorporate a detectable marker. By having multiple hybridization probes having a detectable marker, the signal generated by the hybridization probe hybridizing to the nucleic acid sequence can be amplified, thereby increasing the sensitivity of the method. The use of a composite hybridization probe as the first hybridization probe is described in Example 1.

The first and second hybridization probes may include RNA or DNA sequences such that the complementary nucleic acid sequences formed between the hybridization probes and the target sequence; may be two DNA sequences or a RNA and a DNA sequence.

As illustrated in FIGS. 5 and 7, the second hybridization probe is attached to a second solid support. FIG. 5 illustrates the second hybridization probe being attached to the second solid support after hybridization while FIG. 6 illustrates the second hybridization probe being attached to the second solid support before hybridization. It is preferred, however, that the second hybridization probe be immobilized after hybridization since hybridization is generally more effectively conducted in solution.

When the second hybridization probe is immobilized on the second solid support after hybridization, as illustrated in FIG. 5, it is preferred that the second hybridization probe be attached to the second solid support using a pair of complexing agents where the second hybridization probe includes a third complexing agent that forms a binding pair with a fourth complexing agent on the second solid support, thereby enabling the immobilization of the second hybridization probe onto the second solid support.

As illustrated in FIGS. 5 and 6, once the first set of nucleic acids are contacted with a second hybridization probe and immobilized on a second solid support, any sequences in the first set of nucleic acids that do not become immobilized on the second solid support are separated in a second separation step from those sequences in the first set of nucleic acids that become immobilized, the nucleic acids isolated after the second separation step being hereinafter referred to as the second set of nucleic acids. Separation of the second set of nucleic acids may be accomplished by a variety of methods known in the art including, but not limited to, centrifugation, filtration and washing.

Only those sequences of the first set of nucleic acids that include a o nucleic acid sequence of the second type are isolated as the second set of nucleic acids through immobilization to the second solid support. As discussed above, nucleic acid sequences that do not include a first nucleic acid sequence type do not become immobilized to the first solid support and are eliminated from the sample by the first separation step. Of the first set of nucleic acids isolated by the first separation step, only those sequences which also include a nucleic acid sequence of the second type will be isolated by the second separation step.

The third and fourth complexing agents used to attach the second hybridization probe to the second solid support may be the same pair of complexing agents used with the first hybridization probe and the first solid support. Alternatively, a different pair of complexing agents may be used.

When the same complexing agents are used to attach the first and second hybridization probes to the first and second solid supports, it is preferred that additional steps be taken to prevent the complexing agent on the first hybridization probe from binding to the complexing agent on the second solid support. However, it is preferred that different pairs of complexing agents be used on the first and second hybridization probes. This reduces the chances that the first hybridization probe will become immobilized to the second solid support in the absence of the second hybridization probe. When different complexing agents are used with regard to the first and second hybridization probes, it is preferred that an avidin-biotin binding pair be used in conjunction with the first hybridization probe—first solid support and that a digoxigenin-antidigoxigenin binding pair be used in conjunction with the second hybridization probe—second solid support.

When the same pair of complexing agents is used with the first and the second hybridization probe, for example avidin—biotin, binding of the first hybridization probe to the second solid support can be prevented by blocking the binding site(s) of the complexing agent on the first hybridization probe. For example, excess free first complexing agent can be introduced after the first hybridization probe has been immobilized on the solid support. When biotin is used as the first complexing agent and avidin is used as the second complexing agent, it is further preferred that excess free avidin be introduced after the first hybridization probe has been immobilized in order to block any unbound biotin followed by the introduction of excess free biotin in order to block any unbound avidin binding sites.

The second set of nucleic acids are preferably releasably attached to the second solid support. This enables the second set of nucleic acids immobilized on the second solid support to be released after the second separation step which facilitates the quantification, characterization and/or amplification of the sequences in the second set of nucleic acids. Releasable attachment of the second hybridization probe to the second solid support may be accomplished by the incorporation of a detachable linkage between the second hybridization probe and the second solid support, for example, between the second hybridization probe and the third complexing agent, between the second solid support and the fourth complexing agent, or between the third and fourth complexing agents. Examples of suitable detachable linkages include, but are not limited to the detachable linkers described in Lin, et al., J. Org. Chem. 56:6850–6856 (1991); Ph.D. Thesis of W.-C. Lin, U. C. Riverside, (1990); Hobart, et al., *J. Immunological Methods* 153:93–98 (1992); Jayabaskaran, et al., *Preparative Biochemistry* 17(2): 121–141 (1987); Mouton, et al., *Archives of Biochemistry and Biophysic* 218:101–108 (1982); Funkakoshi, et al., *J. of Chromatography* 638:21–27 (1993); Gildea, et al., *Tetrahedron Letters* 31:7095–7098 (1990); and WO 85/04674, each of which are incorporated herein by reference.

According to the method of the present invention, the first hybridization and immobilization steps enable the immobilization and isolation of nucleic acid sequences having a first nucleic acid sequence type (first set of nucleic acids). Since the second hybridization probe is designed so that it does not hybridize to nucleic acid sequences of the first type, the second hybridization probe only hybridizes to those sequences in the first set of nucleic acids which also include a nucleic acid sequence of the second type. As a result, those sequences in the first set of nucleic acids that become immobilized by hybridization to the second hybridization probe (second set of nucleic acids) will include the nucleic acid sequence aberration for which the first and second hybridization probes are designed to detect.

Detection and quantification of the second set of nucleic acids (i.e., sequences containing a nucleic acid sequence aberration) can be performed using a variety of methods, depending upon the particular first and second hybridization probes used as well as whether a detachable linker is used between the second hybridization probe and the second solid support.

One approach to detecting and quantifying the second set of nucleic acids which include nucleic acid sequence aberrations involves the use of a detectable marker incorporated into the first hybridization probe. According to this embodiment, illustrated in FIGS. 1 and 5, the first set of nucleic acids are released from the first solid support, hybridized to the second hybridization probe and immobilized on a second solid support in such a manner that the first hybridization probe remains hybridized to the first set of nucleic acids during these steps. According to this embodiment, a detectable marker is attached to the; first hybridization probe and is used to indicate the presence of the second set of nucleic acids on the second solid support. The presence of the detectable marker, and hence the first hybridization probe on the second solid support, may be detected either by detecting the detectable marker while attached to the second solid support or after separation from the second solid support.

Any detectable marker that can be attached to or incorporated into a hybridization probe may be used with the first hybridization probe. A detectable marker refers to any molecule, moiety or atom which can be analytically detected and quantified. Methods for detecting detectable markers include, but are not limited to, radioactivity, fluorescence, absorbance, mass spectroscopy, EPR, NMR, XRF, luminescence and phosphorescence. For example, any radiolabel which provides an adequate signal and a sufficient half-life may be used as a detectable marker. Commonly used radioisotopes include $^3$H, $^{14}$C, $^{32}$P and $^{125}$I. In a preferred embodiment, $^{14}$C is used as the detectable marker and is detected by accelerator mass spectroscopy (AMS). $^{14}$C is preferred because of its exceptionally long half-life and because of the very high sensitivity of AMS for detecting 14C isotopes. Other isotopes that may be detected using AMS include, but are not limited to, $^3$H, $^{125}$I, $^{41}$Ca, $^{63}$Ni and $^{36}$Cl.

Fluorescent molecules, such as fluorescein and its derivatives, rhodamine and its derivatives, dansyl, umbeliferone and acridimium, and chemiluminescent molecules such as luciferin and 2,3-dihydrophthalazinediones may also be used as detectable markers. Molecules which bind to a detectable marker may also be covalently attached to or incorporated into hybridization probe, for example, as taught by Ward, European Patent Application No. 63,879 which is incorporated herein by reference. In such instances, the hybridization probe is detected by adding an analytically detectable marker which specifically binds to the probe, thereby enabling detection of the probe. Examples of such molecules and their analytically detectable counterparts include biotin and either fluorescent or chemiluminescent avidin. Antibodies that bind to an analytically detectable antigen may also be used as a detectable marker. The detectable marker may also be a molecule which, when subjected to chemical or enzymatic modification, becomes analytically detectable such as those disclosed in Leary, et al., *Proc. Natl. Acad. Sci. (U.S.A.)*, 80:4045–4049 (1983) which is incorporated herein by reference. Other examples of suitable detectable markers include protein binding sequences which can be detected by binding proteins, such as those disclosed in U.S. Pat. No. 4,556,643 which is incorporated herein by reference.

The first hybridization probe may also itself function as a detectable marker. For example, the first hybridization probe may be separated from the second set of nucleic acids immobilized on the second solid support and isolated, for example by gel electrophoresis.

The detectable marker may be separated from the second solid support by a variety of methods. For example, as illustrated in FIG. 8A, the detectable marker may be separated from the second solid support by treating the sequences immobilized on the second solid support with DNase to digest any DNA immobilized on the solid support. The digested DNA is then collected after digestion and analyzed for the presence of the detectable marker. Alternatively, the nucleic acids attached to the solid support may be removed from the solid support by a variety of chemical and physical methods available, including, for example, treatment with a basic solution (e.g., concentrated NaOH), treatment with an acidic solution and denaturalization of DNA using standard methods such as elevated temperatures or reagents. For example, when the detectable marker used is $^{14}$C, the entire solid support containing the immobilized nucleic acids and hybridization probes may be graphitized and analyzed using accelerator mass spectroscopy (AMS). The use of AMS and a $^{14}$C detectable marker to quantify nucleic acid aberrations is described in greater detail in Example 1.

In another embodiment, illustrated in FIGS. 8B and 8C, the detectable marker is separated from the solid support prior to detection of the detectable marker by dehybridizing the first and/or second hybridization probes from the second set of nucleic acids. This may be done by heating the second solid support to at least 70° C.

By controlling the length of the nucleic acid sequences forming the first and/or second hybridization probes, it is possible to selectively dehybridize the first and second hybridization probes in a particular order. It is also possible to selectively dehybridize the first and second hybridization probes in a particular order by biotinylating one of the hybridization probes and incorporating digoxigenin onto the other hybridization probe. It has been observed that biotinylated probes dehybridize at a lower temperature than hybridization probes containing digoxigenin.

Chromosomal DNA immobilized on the solid support tends to become entangled with one or more strands of chromosomal DNA as well as the solid support. In addition, chromosomal DNA is generally immobilized on the solid support at multiple sites. It is therefore generally preferred to dehybridize the first hybridization probe selectively over the second hybridization probe. When the first hybridization probe is selectively dehybridized over the second hybridization probe, the nucleic acids forming the first hybridization probe may be quantified and thus used as the detectable marker. Quantification of the nucleic acids may be performed by a variety of methods known in the art, preferably by measuring gel electrophoresis, by measuring the absorbance of the nucleic acids using UV spectroscopy, or by quantitative commercial colorimetric methods (e.g. the "DNA DIPSTICK" sold by Invitrogen, San Diego, Calif.).

Selectively dehybridizing the second hybridization probe over the first hybridization probe is desirable in instances where it is sought to isolate nucleic acid containing the nucleic acid sequence aberration. Selectively dehybridizing the first hybridization probe over the second hybridization probe is desirable in instances where it is sought to isolate only the first hybridization probe, for example, in order to use the nucleic acids of the first hybridization probe as a detectable marker. Selectively dehybridizing the first hybridization probe is also desirable where it is sought to maintain the target sequence immobilized onto the solid support in order employ a different hybridization probe on the same sample of nucleic acids.

In another embodiment, illustrated in FIG. 8D, the detectable marker is separated from the solid support prior to detection of the detectable marker by breaking the bond between the second complexing agent and the second solid support. This may be accomplished through the use of a detachable linker positioned between the fourth complexing agent and the second solid support. Examples of suitable detachable rinkages include, but are not limited to the detachable linkers described in Lin, et al., *J. Org. Chem.* 56:6850–6856 (1991); Ph.D. Thesis of W.-C. Lin, U. C. Riverside, (1990); Hobart, et al., *J. Immunological Methods* 153:93–98 (1992); Jayabaskaran, et al., *Preparative Biochemistry* 17(2): 121–141 (1987); Mouton, et al., *Archives of Biochemistry and Biophysics* 218:101–108 (1982); Funkakoshi, et al., *J. of Chromatography* 638:21–27 (1993); Gildea, et al., *Tetrahedron Letters* 31:7095–7098 (1990); and WO 85/04674, each of which are incorporated herein by reference.

In another embodiment, illustrated in FIG. 8E, the detectable marker is separated from the second solid support prior to detection of the detectable marker by breaking the bond between the third and fourth complexing agents. For example, using antidigoxigenin and digoxigenin as the third and fourth binding agents, the bond between the third and fourth complexing agents may be broken.

Figures 8F, 8G:
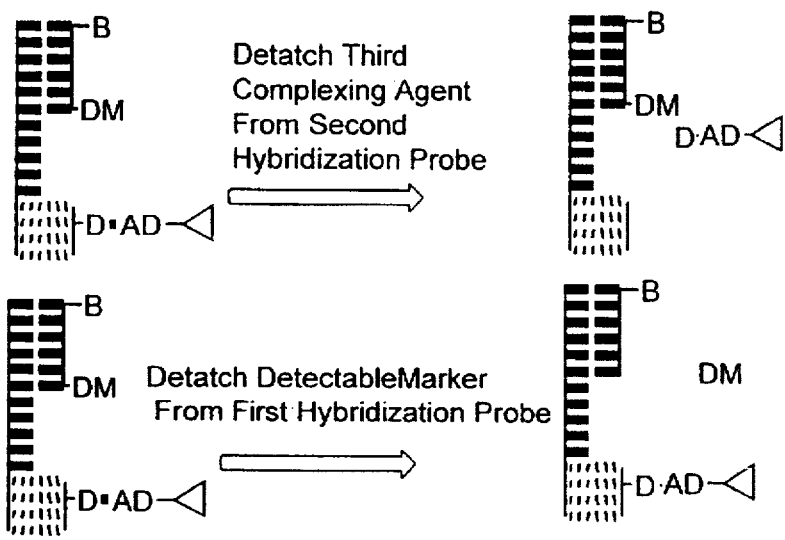

In another embodiment, illustrated in FIG. 8F, the detectable marker is separated from the second solid support prior to detection of the detectable marker by breaking the bond between the third complexing agent and the nucleic acid sequence forming the second hybridization probe. This may be accomplished through the use of a detachable linker positioned between the third complexing agent and the nucleic acid sequence forming the second hybridization probe. Examples of suitable detachable linkages include, but are not limited to the detachable linkers described in the references cited above.

In yet another embodiment, illustrated in FIG. 8G, the detectable marker is separated from the second solid support prior to detection by detaching the detectable marker from the first hybridization probe. This may be accomplished through the use of a detachable linker between the detectable marker and the first hybridization probe. Examples of suitable detachable linkages include, but are not limited to, the detachable linkers described in the references cited above.

The detectable marker may be detected by a variety of methods known in the art, depending on the particular detectable marker employed. For example, AMS may be used when the detectable marker is a radioisotope such as $^{14}C$, liquid scintillation may be used when the detectable marker is tritiated thymidine and standard fluorescence or spectroscopic methods may be used when the detectable marker is a fluorescent molecule or the DNA itself.

A nucleic acid sequence aberration frequency rate may be determined based on the signal generated from the detectable marker using a calibration curve. The calibration curve may be formed by analyzing a sample of cells having a known nucleic acid sequence aberration frequency rate. For example, a calibration curve for the nucleic acid sequence aberration may be generated by analyzing a series of known amounts of cells from a cell line in which the aberration rate of the cell line is known. Alternatively, samples of cells may be analyzed according to the method of the present invention and according to a method known in the art for quantifying a nucleic acid sequence aberration. For example, the FISH method for detecting chromosome translocations may be used to determine the nucleic acid sequence aberration frequency rate of a sample of cells. Then, by serially diluting the sample of cells and assaying the cells according to the method of the present invention, a calibration curve may be generated. Alternative methods for generating a calibration curve are within the level of skill in the art and may be used in conjunction with the method of the present invention.

An alternative approach to detecting and quantifying the second set of nucleic acids which contain nucleic acid sequence aberrations involves the disassociation of the second set of nucleic acids from the second solid support, after which the disassociated second set of nucleic acids are detected and/or quantified, for example by measuring gel electrophoresis, by measuring the absorbance of the nucleic acids using UV spectroscopy, or by quantitative commercial colorimetric methods (e.g. the "DNA DIPSTICK" sold by Invitrogen, San Diego, Calif.).

Detection and/or quantification of the second set of nucleic acids by first disassociating the second set of nucleic acids from the second solid support provides the advantage that the second set of nucleic acids, once disassociated from the second solid support, may be further purified and/or characterized. For example, sequences in the second set of nucleic acids may be further purified by gel electrophoresis, sequenced, or subjected to further hybridization assays. The above-described steps of the present method involving the second hybridization probe and second solid support may also be repeated using different hybridization probes and solid supports. Depending on the amount of nucleic acids obtained, it may also be desirable to amplify the second set of nucleic acids, for example by PCR.

According to the present embodiment of the invention where the second set of nucleic acids are first disassociated from the second solid support, disassociation is preferably achieved using a detachable linker incorporated between the second hybridization probe and the second solid support. For example, as illustrated in FIG. 8D, the second set of nucleic acids are separated from the second solid support by breaking the bond between the fourth complexing agent and the second solid support. This may be accomplished through the use of a detachable linker positioned between the fourth complexing agent and the second solid support. Examples of suitable detachable linkages include, but are not limited to the detachable linkers described in the references cited above.

In another embodiment, illustrated in FIG. 8F, the second set of nucleic acids are separated from the second solid support by breaking the bond between the third and fourth complexing agents. For example, using antidigoxigenin and digoxigenin as the third and fourth binding agents, the bond between the third and fourth complexing agents may be broken.

In another embodiment, illustrated in FIG. 8F, the second set of nucleic acids are separated from the second solid support: by breaking the bond between the third complexing agent and the nucleic acid sequence forming the second hybridization probe. This may be accomplished through the use of a detachable linker positioned between the third complexing agent and the nucleic acid sequence forming the second hybridization probe. Examples of suitable detachable linkages include, but are not limited to the detachable linkers described in the references cited above.

When quantifying the frequency of chromosome translocations in a sample, it is preferred to correct the translocation frequency measured to account for the presence of dicentric chromosomes which can provide a false positive reading. Dicentric chromosomes include the chromosomal DNA from the two chromosomes making up the dicentric chromosome. As a result, depending on the particular hybridization probes used, dicentric chromosomes can be incorrectly measured as translocations.

Dicentric chromosomes are characterized by having two centromeres where each centromere is of a different chromosome type. Dicentric chromosomes may be identified according to the method of the present invention by employing first and second hybridization probes which each hybridize to the centromere of different chromosome. The dicentric chromosome frequency determined may be subtracted from the measured translocation frequency to provide the translocation frequency.

The following example sets forth a method for detecting a chromosome translocation associated with chronic myelogenous leukemia according to the method of the present invention. Further objectives and advantages of the present invention other than those set forth above will become apparent from the example which is not intended to limit the scope of the present invention.

EXAMPLE

1. Detection of a Chromosome Translocation

Chronic myelogenous leukemia (CML) is genetically characterized by the fusion of the bcr and abl genes on chromosomes 22 and 9 respectively to produce a cytogenetically distinct Philadelphia chromosome. In most cases, the fusion also involves a reciprocal translocation between chromosomes 9 and 22. This example provides a method for detecting cells having the distinctive Philadelphia chromosome indicating the presence of chronic myelogenous leukemia.

According to the method of the present invention, the first hybridization probe is formed using the 18-kb phage PEM12 probe (bcr probe) described in Tkachuk, et al., *Science* 250:559–562 (1990) which is incorporated herein by reference. Copies of the first hybridization probe may be generated using PCR as described in Vooijs, et al., *Am. J. Hum. Genet.* 52:586–597 (1993) and chemically modified to incorporate biotinylated uridine as the first complexing agent according to the method of Pinkel, et al., *Proc. Natl. Acad. Sci. (USA)* 83:2934–2938 (1986), each of which is incorporated herein by reference.

The second hybridization probe is formed using the 28-kb cosmid c-H-abl probe (abl probe) described in Tkachuk, et al. Copies of the second hybridization probe are generated using PCR as is described in Vooijs, et al., *Am. J Hum. Genet.* 52:586–597 (1993).

Blood and bone marrow cells from a patient to be tested are isolated according to the procedure described in Tkachuk, et al. DNA from the cell sample is then isolated from the cells using standard methods such as those associated with using the GIBCO BRL TRIzol™ Reagent (Life Technologies, Gaithersburg, Md.), which is incorporated herein by reference. DNA from the cell sample may also be isolated by procedure described in Tkachuk, et al. The isolated DNA is fractionated into small pieces using restriction enzymes or other appropriate methods as described in Pinkel, et al., *Proc. Natl. Acad. Sci. (USA)* 83:2934–2938 (1986).

The first hybridization probe is hybridized to the fractionated DNA sample using the hybridization conditions described in Tkachuk, et al. Once the first hybridization probe has been hybridized to the sample of nucleic acids, a first solid support labelled with avidin is added to immobilize the first hybridization probe by an avidin-biotin linkage. Any nucleic acids hybridized to the first hybridization probe also become immobilized to the solid support. The avidin labelled solid support may be prepared by the methods described in Manning, et al. *Biochemistry* 16:1364–1370 (1977) and Jasiewicz, et al. *Exp. Cell Res.* 100:213–217 (1976), each of which are incorporated herein by reference;.

The first solid support is then washed with cold, pH 7 buffered saline to remove any first hybridization probes and DNA segments which are not immobilized on the first solid support. Remaining immobilized on the first solid support are first set of nucleic acids which are hybridized to the first hybridization probe.

Incorporated onto the first solid support is a detachable linker between the avidin and the first solid support. After the solid support is washed, the avidin molecule is separated from the first solid support, thereby causing the release of the first set of nucleic acids from the first solid support.

The first set of nucleic acids are then hybridized to the second hybridization probe under conditions favorable for hybridization. After hybridization, the hybridized first set of nucleic acids are contacted with a second solid support including a digoxigenin molecule. Binding of the digoxigenin molecule on the second solid support to the antidigoxigenin on the second hybridization probe causes the immobilization of the second hybridization probe to the second solid support as well as any first set of nucleic acids that are hybridized to the second hybridization probe.

The second solid support is then washed with cold, pH 7 buffered saline to remove any second hybridization probes and DNA segments which are not immobilized on the second solid support. Remaining immobilized on the second solid support is a second set of nucleic acids which are hybridized to the second hybridization probe, the sequences in the second set of nucleic acids corresponding to sequences which include the bcr and abl genes.

Incorporated onto the second solid support is a detachable linker between the digoxigenin and the second solid support. After the solid support is washed, the digoxigenin molecule is separated from the second solid support, thereby causing the release of the second set of nucleic acids from the second solid support.

The released second set of nucleic acids are then purified and quantified by gel electrophoresis. A nucleic acid sequence aberration frequency rate may be determined using a calibration curve formed by analyzing a sample of cells having a known nucleic acid sequence aberration frequency rate. For example, a calibration curve for the nucleic acid sequence aberration associated with chronic myelogenous leukemia may be obtained by analyzing a series of known amounts of cells from the K-562 cell line which contain a reciprocal translocation between chromosome 9 and chromosome 22.

Alternatively, samples of cells may be analyzed according to the method of the present invention and according to a method known in the art for quantifying nucleic acid sequence aberrations. Four example the FISH assay method described in Tkachuk, et al. may be used to determine the nucleic acid sequence aberration frequency rate of a sample of cells. Then, by serially diluting the sample of cells and assaying the cells according to the method described in the present example, a calibration curve may be generated. Alternative methods for generating a calibration curve are within the level of skill in the art and may be used in conjunction with the method of the present invention.

2. Improved Method for Isolation and Hybridization of Chromosomes

In order to effectively perform biodosimetry by hybridization of chromosomes in suspension, it is important to have a sample containing a large number of free, hybridized chromosomes. The availability of a large number of free hybridized chromosomes facilitates the sorting of hybridized chromosomes and the detection of bulk chromosomal exchange rearrangement.

Several difficulties exist with regard to hybridizing chromosomes in suspension. For example, hybridization of chromosomes in solution has been hindered by clamping, breakage, and aggregation of chromosomes, leading to large chromosome loss during washing procedures. WO 92108133; Bao-Tram, et al. *Cytometry* 21:111–119 1995.

According to the present method, two additional steps may be taken with regard to standard procedures for chromosome isolation and hybridization in order to reduce chromosome loss so that a large number of good quality metaphase chromosomes are obtained. In the first step, performed during the isolation procedure, chromosomes are treated with RNase in order to decrease cell debris.

The chromosomes are then fixed in a 3:1 solution of methanol: acetic acid prior to hybridization. In order to reduce the viscosity of the chromosome solution (chromosomes in hybridization buffer), the solution is diluted, for example by being mixed 1:1 with solution A (80 mL of 0.15M NaCl/0.015M Na Citrate mixed with 20 mL of double distilled water, pH7) before spinning down the chromosomes.

Hybridization buffers commonly contain a high concentration of dextran sulfate (10% dextran sulfate is standardly used in hybridization buffers) which causes the hybridization buffer to be highly viscous. Applicants believe that the high level viscosity of standard hybridization solutions cause chromosomes to be retained in solution and thus lost during centrifugation. By diluting the hybridization buffer before centrifugation (or by using a more dilute hybridization buffer), the viscosity of the hybridization solution is decreased, thereby lessening the drag on chromosomes during centrifugation and allowing more chromosomes to spin down. As a result, a higher percentage of the chromosomes in solution is recovered. The final concentration of dextran sulfate in the chromosome solution before spin down is preferably less than about 5% and can be decreased even further.

By performing the RNase and dilution steps described above, a much higher percentage of chromosomes in a sample is recovered than is recovered by simply following prior art methods. For example, by recovering chromosomes according to the method described in Cremer, et al., *Human Genetics* 80 235–246 (1988) approximately 0.1 percent of chromosomes in a sample are recovered. By contrast, by modifying the Cremer, et al. method to include the two steps described above, approximately 31–50 percent of chromosomes in a sample are recovered. Table 1 gives the fraction of chromosomes recovered after hybridization in suspension by the method described above and by the Cremer, et al. method.

The 0.1% chromosome yield achieved by the Cremer, et al. method will generally not be sufficient to enable chromosome analysis. The smaller number of chromosomes recovered also cannot compete with methods involving hybridization on slides and is too small for any practical analysis. By contrast, the 30–50 percent chromosome yield achieved by performing the steps described above is approximately 10 times greater than the chromosome yield typically achieved by immobilizing chromosomes on slides for FISH. Furthermore, the total number of chromosomes which are available for analysis by this procedure can be increased simply by increasing the number of chromosomes in the initial sample.

TABLE 1

Fraction of chromosomes recovered after suspension hybridization, determined by fluorescence microscopy.

| METHOD | NUMBER OF CHROMOSOMES[a] | | % CHROMOSOMES RECOVERED | |
|---|---|---|---|---|
| | Initial Number | After Hybridization | Individual[b] | Clump[c] |
| Present Method | $2 \times 10^5$ | 63,000 | 31.5 | 7 |
| | $35 \times 10^5$ | 1,240,000 | 35.4 | 6.7 |
| Cremer, et al. | $2 \times 10^5$ | 234 | 0.117 | 9 |
| | $35 \times 10^{5\ d}$ | — | — | — |

[a]These are single individual chromosomes. The numbers were scaled up from greater than 3,000 chromosomes counted microscopically (except for the 234).
[b]The ratio of individual chromosomes recovered to the number of individual chromosomes before hybridization (no clumps)
[c]The ratio of clumps (small aggregates 3–5 chromosomes) recovered to the number of individual chromosomes after hybridization.
[d]The Cremer, et al. method does not support initial chromosomes numbers greater than $4 \times 10^5$; clumping becomes a severe problem using this method for the larger numbers of chromosomes.

While the present invention is disclosed by reference to the preferred embodiments and example detailed above, it is to be understood that these examples are intended in an illustrative rather than limiting sense, as it is contemplated that modifications will readily occur to those skilled in the art, which modifications will be within the spirit of the invention and the scope of the appended claims.

What is claimed is:

1. A method for detecting nucleic acid aberrations in a sample of chromosomal DNA characterized by a rearrangement which forms a nucleic acid sequence which includes a first sequence unique to a first region of a chromosome, a second sequence unique to a second, different region of the same chromosome or a different chromosome and a region connecting the first and second regions which includes a site of the rearrangement, the method comprising:

a) contacting a first hybridization probe which includes a nucleic acid sequence complementary to the first region with a sample of chromosomal DNA under conditions favorable for hybridization such that the first hybridization probe hybridizes to a first set of chromosomal DNA which include a nucleic acid sequence from the first region;

b) immobilizing the first hybridization probe by forming a linkage attaching the first hybridization probe to a first solid support;

c) after performing steps a-b in any order, releasing the first set of chromosomal DNA from the first solid support;

d) contacting the first set of chromosomal DNA under conditions favorable for hybridization with a second hybridization probe which includes a nucleic acid sequence complementary to the second region, the second hybridization probe hybridizing to a second set of chromosomal DNA which include those chromosomal DNA of the first set which include a nucleic acid sequence from the second region;

e) immobilizing the second hybridization probe by forming a linkage attaching the second hybridization probe to a second solid support, thereby immobilizing the second set of chromosomal DNA; and f) detecting the second set of chromosomal DNA immobilized on the second solid support, the presence of the second set of chromosomal DNA indicating the presence of a nucleic acid sequence aberration without indicating the sequence of the region connecting the first and second regions.

2. The method according to claim 1 wherein the first hybridization probe includes a first complexing agent and the first solid support includes a second complexing agent capable of forming a binding pair with the first complexing agent, the step of immobilizing the first hybridization probe on the first solid support including the step of contacting the first hybridization probe with the first solid support to form a linkage between the first and second complexing agents.

3. The method according to claim 1 wherein the second hybridization probe includes a third complexing agent and the second solid support includes a fourth complexing agent capable of forming a binding pair with the third complexing agent, the step of immobilizing the second hybridization probe on the second solid support including the step of contacting the second hybridization probe with the second solid support to form a linkage between the third and fourth complexing agents.

4. The method according to claim 1 wherein the first hybridization probe is contacted with the sample of chromosomal DNA prior to immobilizing the first hybridization probe to the first solid support.

5. The method according to claim 1 wherein the first hybridization probe is contacted with the sample of chromosomal DNA after immobilizing the first hybridization probe to the first solid support.

6. The method according to claim 1 wherein the second hybridization probe is contacted with the first set of chromosomal DNA prior to releasing the first set of chromosomal DNA from the first solid support.

7. The method according to claim 1 wherein the second hybridization probe is contacted with the first set of chromosomal DNA prior to immobilizing the second hybridization probe to the second solid support.

8. The method according to claim 1 wherein the second hybridization probe is contacted with the first set of chromosomal DNA after immobilizing the second hybridization probe to the second solid support.

9. The method according to claim 1 wherein the nucleic acid sequence aberration is a chromosome translocation, the first region being a region of a first chromosome, the second region being a region of a second, different chromosome.

10. According to claim 2 wherein the first hybridization probe is attached to the first solid support by a linkage which is detachable, the step of releasing the first set of chromosomal DNA from the first solid support including detaching the detachable linkage.

11. The method according to claim 10 wherein the detachable linkage is positioned between the first complexing agent and the first hybridization probe.

12. The method according to claim 10 wherein the detachable linkage is positioned between the first complexing agent and the second complexing agent.

13. The method according to claim 10 wherein the detachable linkage is positioned between the second complexing agent and the first solid support.

14. The method according to claim 1 wherein the linkage attaching the second hybridization probe is attached to the second solid support by a linkage which is detachable, the method further including the step of releasing the second set of chromosomal DNA from the second solid support.

15. The method according to claim 14 wherein the step of releasing the second set of chromosomal DNA from the second solid support is performed prior to detection of the second set of chromosomal DNA.

16. The method according to claim 14 wherein the second hybridization probe is attached to the second solid support by a linkage which is detachable, the, step of releasing the second set of chromosomal DNA from the second solid support including detaching the detachable linkage.

17. The method according to claim 14 wherein the second hybridization probe includes a third complexing agent and the second solid support includes a fourth complexing agent capable of forming a binding pair with the third complexing agent, the step of immobilizing the second hybridization probe on the second solid support including the step of contacting the second hybridization probe with the second solid support to form a linkage between the third and complexing agents, the second hybridization probe being attached to the second solid support by a linkage which is detachable, the step of releasing the second set of chromosomal DNA from the second solid support including detaching the detachable linkage.

18. The method according to claim 17 wherein the detachable linkage is positioned between the third complexing agent and the second hybridization probe.

19. The method according to claim 17 wherein the detachable linkage is positioned between the third complexing agent and the fourth complexing agent.

20. The method according to claim 17 wherein the detachable linkage is positioned between the fourth complexing agent and the second solid support.

21. The method according to claim 1 wherein the first hybridization probe includes a detectable marker, the step of detecting the second set of chromosomal DNA including detecting the detectable marker.

22. The method according to claim 21 wherein the step of detecting the detectable marker includes detaching the first complexing agent and the first hybridization probe to release the detectable marker from the second solid support, and detecting any detectable marker released from the second solid support.

23. The method according to claim 21 wherein the step of detecting the detectable marker includes the steps of dehybridizing the first hybridization probe from the second set of chromosomal DNA, and detecting any detectable marker released from the second solid support.

24. The method according to claim 21 wherein the step of detecting the detectable marker includes the steps of dehybridizing the second hybridization probe from the second set of chromosomal DNA to release the detectable marker from the second solid support, and detecting any detectable marker released from the second solid support.

25. The method according to claim 21 wherein the step of detecting the detectable marker includes detaching the detectable marker from the first hybridization probe to release the detectable marker from the second solid support, and detecting any detectable marker released from the second solid support.

26. The method according to claim 1 wherein the step of detecting the second set of chromosomal DNA includes the step of releasing the second set of chromosomal DNA from the second solid support.

27. The method according to claim 26 wherein the step of detecting the second set of chromosomal DNA includes the step of detecting the released second set of chromosomal DNA spectroscopically.

28. The method according to claim 26 wherein the step of detecting the second set of chromosomal DNA includes the step of amplifying the released second set of chromosomal DNA.

29. The method according to claim 26 including the step of detecting the second set of chromosomal DNA includes purifying the released second set of chromosomal DNA by gel electrophoresis.

30. A method for detecting nucleic acid aberrations in a sample of chromosomal DNA characterized by a rearrangement which forms a nucleic acid sequence which includes a first sequence unique to a first region of a chromosome, a second sequence unique to a second, different region of the same chromosome or a different chromosome and a region connecting the first and second regions which includes a site of the rearrangement, the method comprising:

a) contacting a sample of chromosomal DNA under conditions favorable for hybridization with a first hybridization probe which includes a nucleic acid sequence complementary to a nucleic acid sequence from the first region with a sample of chromosomal DNA such that the first hybridization probe hybridizes to a first set of chromosomal DNA which include a nucleic acid sequence from the first region;

b) contacting the sample of chromosomal DNA under conditions favorable for hybridization with a second hybridization probe which includes a nucleic acid sequence complementary to a nucleic acid sequence from the second region such that the second hybridization probe hybridizes to those chromosomal DNA which include a nucleic acid sequence from the second region;

c) immobilizing the first hybridization probe by forming a linkage attaching the first hybridization probe to a first solid support;

d) after performing steps a, b and c in any order, releasing the first set of nucleic acids from the first solid support;

e) immobilizing a second set of chromosomal DNA which include those chromosomal DNA of the first set to which the second hybridization probe is hybridized by forming a linkage attaching the second hybridization probe to a second solid support; and f) detecting the second set of chromosomal DNA immobilized on the second solid support, the presence of the second set of chromosomal DNA indicating the presence of a nucleic acid sequence aberration without indicating the sequence of the region connecting the first and second regions.

31. The method according to claim 30 wherein the nucleic acid sequence aberration is a chromosome translocation, the first region being a region of a first chromosome, the second region being a region of a second, different chromosome.

32. A method for diagnosing a disease in a sample of chromosomal DNA, the occurrence of which is associated with the presence of a nucleic acid sequence aberration characterized by a rearrangement which forms a nucleic acid sequence which includes a first sequence unique to a first region of a chromosome, a second sequence unique to a second, different region of the same chromosome or a different chromosome and a region connecting the first and second regions which includes a site of the rearrangement, the method comprising:

a) contacting a first hybridization probe including a nucleic acid sequence complementary to a nucleic acid sequence from the first region with a sample of chromosomal DNA under conditions favorable for hybridization such that the first hybridization probe hybridizes to a first set of chromosomal DNA which include a nucleic acid sequence from the first region;

b) immobilizing the first hybridization probe by forming a linkage attaching the first hybridization probe to a first solid support;

c) after performing steps a-b in any order, releasing the first set of chromosomal DNA from the first solid support;

d) contacting the first set of chromosomal DNA under conditions favorable for hybridization with a second hybridization probe which includes a nucleic acid sequence complementary to a nucleic acid sequence from the second region, the second hybridization probe hybridizing to a second set of chromosomal DNA which include those chromosomal DNA of the first set which include a nucleic acid sequence from the second region;

e) immobilizing the second hybridization probe by forming a linkage attaching the second hybridization probe to a second solid support, thereby immobilizing a second set of chromosomal DNA; and f) diagnosing the disease by detecting the second set of chromosomal DNA immobilized on the second solid support, the presence of the second set of chromosomal DNA indicating the presence of the nucleic acid sequence aberration associated with the disease without indicating the sequence of the region connecting the first and second regions.

33. The method according to claim 32 wherein the disease is a cancer selected from the group consisting of leukemia, lymphoma, melanoma, prostate cancer and cervical cancer.

34. The method according to claim 32 wherein the first or second region is an oncogene nucleic acid sequence.

35. A kit for detecting nucleic acid sequences which include a nucleic acid aberration characterized by a rearrangement which forms a nucleic acid sequence which includes a first sequence unique to a first region of a chromosome, a second sequence unique to a second, different region of the same chromosome or a different chromosome and a region connecting the first and second regions which includes a site of the rearrangement, the kit comprising:

a) a first hybridization probe including a nucleic acid sequence complementary to a nucleic acid sequence from the first chromosome region such that the first hybridization probe hybridizes to chromosomal DNA which include a nucleic acid sequence from the first chromosome region and including a first complexing agent capable of attaching to a second complexing agent; and b) a second hybridization probe including a detectable marker and a nucleic acid sequence complementary to a nucleic acid sequence from the second chromosome region such that the second hybridization probe hybridizes to chromosomal DNA in the sample which include a nucleic acid sequence from the second chromosome region and including a third complexing agent capable of attaching to a fourth complexing agent;

wherein the hybridization of the first and second hybridization probes to chromosomal DNA indicates the presence of a nucleic acid aberration without indicating the sequence of the region connecting the first and second regions and wherein at least one of the first and second hybridization probes is a composite probe of at least a region of a chromosome.

36. The kit according to claim 35, the kit further comprising the second complexing agent attached to a first solid support.

37. The kit according to claim 36, the kit further comprising the fourth complexing agent attached to a second solid support.

38. The method according to claim 1 wherein at least one of the first and second hybridization probes is a composite probe of at least a portion of a chromosome.

39. The method according to claim 1 wherein the first and second hybridization probes are a composite probe of at least a portion of a chromosome.

40. The method according to claim 30 wherein at least one of the first and second hybridization probes is a composite probe of at least a portion of a chromosome.

41. The method according to claim 30 wherein the first and second hybridization probes are a composite probe of at least a portion of a chromosome.

42. The method according to claim 32 wherein at least one of the first and second hybridization probes is a composite probe of at least a portion of a chromosome.

43. The method according to claim 32 wherein the first and second hybridization probes are a composite probe of at least a portion of a chromosome.

44. The kit according to claim 35 wherein at least one of the first and second hybridization probes is a composite probe of a whole chromosome.

45. The kit according to claim 35 wherein the first and second hybridization probes are composite probes of different whole chromosomes.

* * * * *